US008242146B2

(12) United States Patent
Klein et al.

(10) Patent No.: US 8,242,146 B2
(45) Date of Patent: Aug. 14, 2012

(54) COMBINATION OF A NSAID AND A PDE-4 INHIBITOR

(75) Inventors: Thomas Klein, Constance (DE); Hans-Peter Kley, Allensbach (DE)

(73) Assignee: Nycomed GmbH, Constance (DE)

( * ) Notice: Subject to any disclaimer, the term of this patent is extended or adjusted under 35 U.S.C. 154(b) by 1207 days.

(21) Appl. No.: 12/003,129

(22) Filed: Dec. 20, 2007

(65) Prior Publication Data

US 2008/0255209 A1    Oct. 16, 2008

Related U.S. Application Data

(62) Division of application No. 10/489,920, filed as application No. PCT/EP02/10424 on Sep. 17, 2002, now abandoned.

(51) Int. Cl.
*A61K 31/44* (2006.01)
(52) U.S. Cl. ...................................................... 514/352
(58) Field of Classification Search ........................ None
See application file for complete search history.

(56) References Cited

U.S. PATENT DOCUMENTS

| 4,736,024 | A | 4/1988 | Della Valle et al. | |
|---|---|---|---|---|
| 6,174,878 | B1 | 1/2001 | Gamache et al. | 514/211.12 |
| 6,410,563 | B1 | 6/2002 | Deschenes et al. | |

FOREIGN PATENT DOCUMENTS

| CA | 2009730 A1 | 8/1990 |
|---|---|---|
| WO | 99/06404 A1 | 2/1999 |
| WO | 99/23077 A1 | 5/1999 |
| WO | 01/00229 A1 | 1/2001 |
| WO | 01/13953 A2 | 3/2001 |
| WO | 01/32127 A2 | 5/2001 |
| WO | 01/47880 A1 | 7/2001 |
| WO | 01/57036 A1 | 8/2001 |
| WO | 01/58441 A1 | 8/2001 |
| WO | 02/060896 A1 | 8/2002 |
| WO | 02/064584 A1 | 8/2002 |

OTHER PUBLICATIONS

Bundschuh, D.S. et al., "In Vivo Efficacy in Airway Disease Models of Roflumilast, a Novel Orally Active PDE4 Inhibitor", *Journal of Pharmacology and Experimental Therapeutics*,vol. 297, No. 1, pp. 280-290, (2001).
Dyke, H.J., "Update on the therapeutic potential of PDE4 inhibitors", *Expert Opin. Investig. Drugs*, vol. 11, No. 1, pp. 1-13, (2002).
Germann, P. et al., "Experimental approaches for the treatment of the acute respiratory distress syndrome in a rat lung lavage model", *Recent Res. Devel. Resp. Critical Care Med.*, vol. 1, pp. 161-179, (2001).
Norman, P., "PDE4 inhibitors 2001. Patent and literature activity 2000—Sep. 2001", *Expert Opin. Ther. Patents*, vol. 12, No. 1, pp. 93-111, (2002).
Suttorp, N. et al., "Phosphodiesterasen—Inhibition und pulmonale Strombahn—ein neuer Therapieansatz?", *Atemwegs und Lungenkrankheiten*, vol. 22, No. 11, pp. 560-566, (1996).

Wolda, S.L., "PDE4 inhibitors and chronic obstructive pulmonary disease", Emerging Drugs, vol. 5, No. 3, pp. 309-319, (2000).
Silva, J.C.R. et al., "Effects of pentoxifylline and nabumetone on the serum levels of IL-1β and TNF α in rats with adjuvant arthritis", Inflammation Research, vol. 49, pp. 14-19, (2000).
Kumar, A. et al., "Analgesic and anti-inflammatory effects of phosphodiesterase inhibitors", *Indian Journal of Experimental Biology*, vol. 38, pp. 26-30, (2000).
Reuter, B.K. et al.,"Phosphodiesterase inhibitors prevent NSAID entreopathy independently of effects on TNF-α release", *Am J Physiol*, vol. 277, pp. G847-G854, (1999).
Sivola, J. et al., "Effects of nonsteroidal anti-inflammatory drugs on rat gastric mucosal phosphodiesterase activity", *Agents and Actions*, vol. 12, No. 4, pp. 516-520, (1982).
Salcedo, J. et al., "Phosphodiesterase 4 Inhibition, A New Mechanism to Maintain and Promote Gastric and Intestinal Mucosal Integrity Against NSAID-Induced Injury in the Rat", Gastroenterology, vol. 114, No. 4, pp. G1126, Abstract.
Tariq, M. et al., "Gastric Antiulcer and cytoprotective effects of Dipyridamole in rats", *J. Pharmacol. Exp. Ther.*, vol. 253, No. 3, pp. 944-949 (1990), Abstract 113:71071 American Chemical Society.
Bertrand, et al., "Increase in tumor necrosis factor-α production linked to the toxicity of indomethacin for the rat small intestine", British Journal of Pharmacology, vol. 124, pp. 1385-1394, (1998).
Bouchier-Hayes, et al., "Comparison of the efficacy and tolerability of diclofenac gel (Voltarol Emulgel) and felbinac gel (Traxam) in the treatment of soft tissue injuries", BJCP, vol. 44, No. 8, pp. 319-320, (1990).
Diaz-Granados, et al., "Dextran Sulfate Sodium-Induced Colonic Histopathology, but not Altered Epithelial Ion Transport, Is Reduced by Inhibition of Phosphodiesterase Activity", American Journal of Pathology, vol. 156, No. 6, pp. 2169-2177, (2000).
Ding, et al., "Prostaglandin, tumor necrosis factor α and neutrophils: causative relationship in indomethacin-induced stomach injuries", European Journal of Pharmacology, vol. 348, pp. 257-263, (1998).
Gomez, et al., "Effect of Topical Diflumidone on Ultraviolet-Light-Induced Erythema", Dermatologica, vol. 162, pp. 175-182 (1981).
Häfner, et al., "Additive Effects of Phosphodiesterase-4 Inhibition on Effects of rSP-C Surfactant", Am J Respir Crit Care Med, vol. 161, pp. 1495-1500, (2000).
Hartmann, et al., "Specific Type IV Phosphodiesterase Inhibitor Rolipram Mitigates Experimental Colitis in Mice", The Journal of Pharmacology and Experimental Therapeutics, vol. 292, No. 1, pp. 22-30, (2000).
Hatzelmann, et al., "Anti-Inflammatory and Immunomodulatory Potential of the Novel PDE4 Inhibitor Roflumilast in Vitro", The Journal of Pharmacology and Experimental Therapeutics, vol. 297, No. 1, pp. 267-279, (2001).

*Primary Examiner* — Tracy Vivlemore
*Assistant Examiner* — Jennifer Berrios
(74) *Attorney, Agent, or Firm* — The Nath Law Group; Sheldon M. McGee

(57) ABSTRACT

The invention relates to the combined use of a PDE4 inhibitor and a conventional NSAID in the treatment of an inflammatory disease and/or an inflammation-associated disorder while minimizing gastrointestinal side effects, such as gastric erosions and ulcer, which are frequently associated with the use of conventional NSAIDs. A preferred PDE 4 inhibitor for this combination is roflumilast or a derivative thereof. A preferred conventional NSAID for this combination is diclofenac or a derivative thereof.

4 Claims, No Drawings

COMBINATION OF A NSAID AND A PDE-4 INHIBITOR

This application is a divisional of U.S. Ser. No. 10/489,920, filed Mar. 18, 2004 now abandoned, which is a 371 of PCT/EP02/10424 filed Sep. 17, 2002, and which claims benefit of priority to EP01000473.7 filed Sep. 19, 2001, the disclosure of which is incorporated herein by reference in its entirety for all purposes.

FIELD OF APPLICATION OF THE INVENTION

The invention relates to the combination of certain known active compounds for therapeutic purposes.

The substances used in the combination according to the invention are known active compounds from the PDE4-inhibitor class and active compounds from the non-steroidal anti-inflammatory drug (NSAID) class.

KNOWN TECHNICAL BACKGROUND

In the International Patent Application WO01/58441 the treating of an inflammatory disease by administering a phosphodiesterase 4 inhibitor in combination with an inhibitor of prostaglandin synthesis, NSAIDS being exemplary, is disclosed.

DESCRIPTION OF THE INVENTION

The use of nonsteroidal anti-inflammatory drugs (NSAIDs) is often associated with the development of gastrointestinal (GI) side effects such as gastric erosions and ulcer, which limit their widespread clinical use.

Investigations into the role of several NSAIDs in inhibiting the phosphodiesterase 4 and 5 in vitro showed that in partially purified or recombinant PDE4 and PDE5, NSAIDs with preferential COX-2 selectivity (for example, nimesulide [INN], CGP28238 [Research Code], L-745337 [Research Code], and the highly selective drug celecoxib [INN]) possess PDE4 and PDE5 activity in the μM range, whereas conventional NSAIDs (for example, acetylsalicylic acid, diclofenac [INN] or indometacin [INN]) show only minor effects.

In isolated guinea pig Langendorff hearts, celecoxib selectively increased coronary heart flow at doses consistent with its inhibitory potency on PDE4 and 5, but had no effect on left ventricular pressure and heart rate, thereby excluding inhibition of PDE3.

In mice, diclofenac (3-100 mg/kg, p.o.) induced gastrointestinal bleeding ($ED_{50}$=56 mg/kg), assessed by spectrophotometric determination of fecal hemoglobin. Treatment with diclofenac (10-100 mg/kg, p.o. t=0 h) in the presence of the selective PDE5 inhibitor sildenafil (3-100 mg/kg, p.o. t=−48 h to +7 h) demonstrated no protection from NSAID-induced blood loss, whereas treatment in the presence of several selective PDE4 inhibitors significantly reduced the amount of detectable hemoglobin.

In summary, one can say that NSAIDs with preferential COX-2 selectivity possess PDE4 and PDE5 inhibitory potency on isolated enzymes, an effect which was confirmed in the Langendorff heart by an increase in coronary flow. It seems that the intrinsic PDE4—but not the intrinsic PDE5—inhibitory component of NSAIDs with preferential COX-2 selectivity most likely contribute to the gastrointestinal safety of these drugs. Furthermore, gastrointestinal side effects of conventional NSAIDs can be attentuated or even prevented, if these class of compounds is applied in combination with a compound from the class of selective PDE4 inhibitors.

The invention thus relates to the combined use of a PDE4 inhibitor and a conventional NSAID in the treatment of an inflammatory disease and/or an inflammation-associated disorder while minimizing gastrointestinal side effects, such as gastric erosions and ulcer, which are frequently associated with the use of conventional NSAIDs.

"Combined use" in the context of the invention means the simultaneous, sequential or separate ad-ministration of the conventional NSAID on the one hand and of the PDE4 inhibitor on the other hand.

Simultaneous administration includes—aside from the simultaneous uptake of two separate dosage forms containing the conventional NSAID in the one and the PDE4 inhibitor in the other dosage form—pharmaceutical compositions containing both active ingredients in one single dosage form (fixed unit dose form).

Simultaneous administration also includes the oral administration of the PDE4 inhibitor during i.v. administration (e.g. by infusion) of the conventional NSAID, or shortly after intramuscular or intravenous injection of the conventional NSAID.

Sequential administration in the context of the invention means the administration of the conventional NSAID on the one hand and of the PDE4 inhibitor on the other hand in separate dosage forms within less than 12 hours, more preferably within less than one hour, most preferably within 5 minutes or less, including regimen where the PDE4 inhibitor is administered first.

Separate administration within the context of the invention means the administration of the conventional NSAID on the one hand and of the PDE4 inhibitor on the other hand in separate dosage forms within 12 hours or more, including administration regimen where the PDE4 inhibitor is administered first, and including regimen where e.g. the conventional NSAID is administered twice or three times daily and the PDE4 inhibitor is administered once or twice daily.

Sequential and separate administration also include the oral administration of the PDE4 inhibitor and the i.v. administration (e.g. by infusion) or intramuscular or intravenous injection of the conventional NSAID.

"Combined use" in the context of the invention also includes a pharmaceutical product comprising both the conventional NSAID and the PDE4 inhibitor as discrete separate dosage forms, in separate containers or e.g. in blisters containing both types of drugs in discrete solid dosage units, preferably in a form in which the dosage units which have to be taken together or which have to be taken within one day are grouped together in a manner which is convenient for the patient. Said pharmaceutical product itself or as a part of a kit may contain instructions for the simultaneous, sequential or separate administration of the discrete separate dosage units, to a patient in need thereof.

By the expression "PDE4 inhibitor" is meant a phosphodiesterase inhibitor, which selectively inhibits the type 4 phosphodiesterase when compared to other known types of phosphodiesterase, e.g. type 1, 2, 3, 5 etc., whereby the compound has a lower $IC_{50}$ (more potent) for the type 4 phosphodiesterase, such as where the $IC_{50}$ for PDE4 inhibition is about factor 100 lower compared to $IC_{50}$ for inhibition of other known type of phosphodiesterase, e.g. type 1, 2, 3, 5 etc.

By "conventional NSAID" is meant a cyclooxygenase inhibitor which inhibits both, the constitutive form (COX-1) and the inducible form (COX-2) of the cyclooxygenase and does not contain any of the following residues: —S(O)$_2$NH$_2$, —S(O)$_2$CH$_3$, —S(O)$_2$N(H)C(O)CH$_2$CH$_3$ and —N(H)—S(O)$_2$—CH$_3$.

PDE4 inhibitors within the meaning of the present invention are those which are named expressis verbis as an example or described and/or claimed generically in the following patent applications and patents: EP0428302, EP0731099, WO9212961, WO9319749, WO9402465, WO9500516, WO9501338, WO9611690, WO9603399, WO9636625, WO9636626, WO9723457, WO9728131, WO9735854, WO9743288, WO9807715, WO9808841, WO9809946, WO9821207, WO9821209, WO9822453, WO9831674, WO9905111, WO9905112, WO9905113, WO9931090, WO9957115, WO9964414, WO0001695, WO0026208, WO0042017, WO0042018, WO0042019, WO0042020, WO0042034, WO0130766, WO0130777, WO0151470, WO0206239, WO0206270, WO0205616 and WO0206238 and additionally the following compounds identified by their research codes: CDC-998, D-4396, IC-485, CC-1088 and KW-4490. Substances having good oral availability are preferred here.

Preferred PDE4 inhibitors which are selected from the above-defined PDE4 inhibitors are the compounds with the research codes CDC-998, SH-636, D-4396, IC-485, CC-1088 and 3,5-dichloro-4-[8-methoxy-2-(trifluoromethyl)quinoline-5-ylcarboxamido]pyridine-1-oxide [Research Code: SCH351591], 3-[3-(cyclopentyloxy)-4-methoxybenzyl]-6-(ethylamino)-8-isopropyl-3H-purine [Research-Code: V 11294A], N-[9-methyl-4-oxo-1-phenyl-3,4,6,7-tetrahydropyrrolo[3,2,1-jk][1,4]benzo-diazepin-3 (R)-yl]pyridine-4-carboxamide [Research-Code: CI-1018, N-(3,5-dichloro-4-pyridinyl)-2-[1-(4-fluorobenzyl)-5-hydroxy-1H-indol-3-yl]-2-oxoacetamide [Research-Code: AWD-12-281], N-(3,5-dichloropyridin-4-yl)-2-[5-fluoro-1-(4-fluorobenzyl)-1H-indol-3-yl]-2-oxoacetamide [Research-Code: AWD-12-343], 8-Amino-1,3-bis(cyclopropylmethyl) xanthine [INN: CIPAMFYLLINE], Tetrahydro-5-[4-methoxy-3-[(1S,2S,4R)-2-norbornyloxy]phenyl]-2(1H)-pyrimidone [INN: ATIZORAM], β-[3-(Cyclopentyloxy)-4-methoxyphenyl]-1,3-dihydro-1,3-dioxo-2H-isoindole-2-propanamide [Research-Code: CDC-801], Methanesulfonic acid 2-(2,4-dichlorophenylcarbonyl)-3-ureidobenzo-furan-6-yl ester [INN: LIRIMILAST], N-(3,5-dichloropyrid-4-yl)-3-cyclopentyloxy-4-methoxybenzamide [INN: PICLAMILAST], cis-[4-Cyano-4-(3-cyclopentyloxy-4-methoxyphenyl)cyclohexane-1-carboxylic acid [INN: CILOMILAST] and 3-Cyclopropylmethoxy-4-difluoromethoxy-N-(3,5-dichloropyrid-4-yl)-benzamide [INN: ROFLUMILAST].

Particularly preferred PDE4-inhibitors are cis-[4-Cyano-4-(3-cyclopentyloxy-4-methoxyphenyl)cyclohexane-1-carboxylic acid [INN: CILOMILAST] and 3-Cyclopropylmethoxy-4-difluoromethoxy-N-(3,5-di-chloropyrid-4-yl)-benzamide [INN: ROFLUMILAST].

Conventional NSAIDs within the meaning of the present invention are glycolic acid [o-(2,6-dichloroanilino)phenyl] acetate(ester) [INN: ACECLOFENAC]; 1-(4-chlorobenzoyl)-5-methoxy-2-methyl-1H-indole-3-acetic acid carboxymethyl ester [INN: ACEMETACIN]; 2-(acetyloxy) benzoic acid [ACETYLSALICYLIC ACID], 2-methoxyphenyl-alpha-methyl-4-(isobutyl)phenylacetate [Research Code: AF-2259], (4-allyloxy-3-chlorophenyl)acetic acid [INN: ALCLOFENAC], p-[(2-methylallyl)amino] hydratropic acid [INN: ALMINOPROFEN], 2-amino-3-benzoylphenylacetic acid [INN: AMFENAC], (plus/minus)-4-(1-hydroxyethoxy)-2-methyl-N-2-pyridyl-2H-1,2-benzothiazine-3-carboxamide ethylcarbonate (ester), 1,1-dioxide [INN: AMPIROXICAM], 2-methoxyphenyl-1-methyl-5-(p-methylbenzoyl)pyrrol-2-acetamido-acetate [INN: AMTOLMETINGUACIL], (plus/minus)-2,3-dihydro-5-(4-methoxybenzoyl)-1H pyrrolizine-1-carboxylic acid [INN: ANIROLAC], 2-[4-(alpha,alpha,alpha-trifluoro-m-tolyl)-1-piperazinyl]ethyl-N-(7-trifluoromethyl-4-quinolyl) anthranilate [INN: ANTRAFENINE], 5-(dimethylamino)-9-methyl-2-propyl-1H-pyrazolo[1,2-a][1,2,4]benzo-triazine-1,3(2H)-dione [INN: AZAPROPAZONE], 4-acetamidophenyl salicylate acetate [INN: BENORILATE], 2-(8-methyl-10,11-dihydro-11-oxodibenz[b,f]oxepin-2-yl) propionic acid [INN: BERMOPROFEN], 2-[(1-benzyl-1H-indazol-3-yl)methoxy]-2-methylpropionic acid [INN: BINDARIT], [2-amino-3-(p-bromobenzoyl)phenyl]acetic acid [INN: BROMFENAC], 3-(3-chloro-4-cyclohexylbenzoyl) propionic acid [INN: BUCLOXIC ACID], 5-butyl-1-cyclohexylbarbituric acid [INN: BUCOLOM], 4-butoxy-N-hydroxybenzeneacetamide [INN: BUFEXAMAC], butylmalonic acid mono(1,2-diphenylhydrazide) [INN: BUMADIZONE], alpha-ethyl-4-(2-methylpropyl)benzeneacetic acid [INN: BUTIBUFEN], 2-(4-biphenylyl)butyric acid, trans-4-phenylcyclohexylamine-salt (1:1) [INN: BUTIXIRATE], 2-(acetyloxy)-benzoic acid, calcium salt, compound with urea (1:1) [INN: CARBASALATE CALCIUM], (plus/minus)-6-chloro-alpha-methylcarbazole-2-acetic acid [INN: CARPROFEN], 1-cinnamoyl-5-methoxy-2-methylindole-3-acetic acid [INN: CINMETACIN], N-(2-pyridyl)-2-methyl-4-cinnamoyloxy-2H-1,2-benzothiazine-3-carboxamide-1,1-dioxide [INN: CINNOXICAM], 6-chloro-5-cyclohexyl-1-indancarboxylic acid [INN: CLIDANAC], 2-[4-(p-chlorophenyl)benzyloxy]-2-methylpropionic acid [INN: CLOBUZARIT], 5-methoxy-2-methyl-3-indolylacetohydroxamic acid [INN: DEBOXAMET], (S)-(+)-p-isobutylhydratropic acid [INN: DEXIBUPROFEN], (+)-(S)-m-benzoylhydratropic acid [INN: DEXKETOPROFEN], 2-[(2,6-dichlorophenyl)amino]benzeneacetic acid [INN: DICLOFENAC], 2',4'-Difluoro-4-hydroxy-3-biphenylcarboxylic acid [INN: DIFLUNISAL], 4-(2,6-dichloroanilino)-3-thiopheneacetic acid [INN: ELTENAC], N-beta-phenethyl-anthranilic acid [INN: ENFENAMIC ACID] salicylic acid acetate, ester with beta-hydroxy p-acetophenetide. [INN: ETERSALATE], 1,8-diethyl-1,3,4,9-tetrahydropyrano[3,4-b]indole-1-acetic acid [INN: ETODOLAC], 2-[[3-(trifluoromethyl)phenyl]amino] benzoic acid 2-(2-hydroxyethoxy)-ethyl ester [INN: ETOFENAMATE], p-chlorobenzoic acid, ester with 4-butyl-4-(hydroxymethyl)-1,2-diphenyl-3,5-pyrazolidinedione [INN: FECLOBUZONE], 4-biphenylacetic acid [INN: FELBINAC], 3-(4-biphenylylcarbonyl)propionic acid [INN: FENBUFEN], [o-(2,4-dichlorophenoxy)phenyl]acetic acid [INN: FENCLOFENAC], (plus/minus)-m-phenoxyhydratropic acid [INN: FENOPROFEN], 4-(p-chlorophenyl)-2-phenyl-5-thiazoleacetic acid [INN: FENTIAZAC], (plus/minus)-alpha-[[(2-hydroxy-1,1-dimethylethyl)amino]methyl]-benzyl alcohol [INN: FEPRADINOL], 4-(2',4'-difluorobiphenylyl)-4-oxo-2-methylbutanoic acid [INN: FLOBUFEN], N-(alpha,alpha,alpha-trifluoro-m-tolyl)anthranilic acid [INN: FLUFENAMIC ACID], (plus)-2-(p-fluorophenyl)-alpha-methyl-5-benzoxazoleacetic acid [INN: FLUNOXAPROFEN], 2-fluoro-alpha-methyl-4-biphenylacetic acid [INN: FLURBIPROFEN], (plus/minus)-2-(2-fluoro-4-biphenylyl)propionic acid 1 (acetoxy)ethyl ester [INN: FLURBIPROFEN AXETIL], 2-ethyl-2,3-dihydro-5-benzofuranacetic acid [INN: FUROFENAC], 2-[4-(2'-furoyl)phenyl]propionic acid [INN: FURPROFEN], 2-[2-[1-(p-chlorobenzoyl)-5-methoxy-2-methylindol-3-ylacetamido]-2-deoxy-D-glucose [INN: GLUCAMETACIN], 2-(2-fluorobiphenyl-4-yl)propionic acid 4-nitrooxybutylester [Research Code: HCT-1026], (p-isobutylphenyl)acetic acid [INN: IBUFENAC], alpha-p-isobutylphenylpropionic acid [INN: IBUPROFEN], methyl 4-(3-thienyl)phenyl-alpha-methylacetate [Research Code: IDPH-8261], (plus/minus)-2-[p-(1-oxo-2-isoindolinyl)phenyl]butyric acid [INN: INDOBUFEN], 1-(4-chlorobenzoyl)-5-methoxy-2-methyl-1H-indole-3-acetic acid [INN: INDOMETACIN], 1-(4-chlorobenzoyl)-5-methoxy-2-methyl-1H-indole-3-acetic acid, 3,7,11-trimethyl-2,6,10-dodecatrienyl ester [INN: INDOMETACIN FARNESIL], p-(1-oxo-2-isoindolinyl)hydratropic acid [INN: INDOPROFEN], 2-(10-methoxy-4H-benzo[4,5]-cyclohepta[1,2-b]thiophen-4-ylidene)-acetic acid [Research Code: IX-207-887], m-benzoylhydratropic acid [INN: KETOPROFEN], (DL)-5-benzoyl-3H-1,2-dihydropyrrolo[1,2-a]pyrrole-1-carboxylic acid [INN: KETOROLAC], 2,3-dihydro-5-hydroxy-6-[2-(hydroxymethyl)cinnamyl]benzofuran [Research Code: L-651896], N-(2-carboxyphenyl)-4-chloroanthranilic acid [INN: LOBENZARIT], 3-(p-chlorophenyl)-1-phenylpyrazole-4-acetic acid [INN: LONAZOLAC], 6-chloro-4-hydroxy-2-methyl-N-2-pyridyl-2H-thieno-[2,3-e]-1,2-thiazine-3-carboxamide 1,1-dioxide [INN: LORNOXICAM], 2-[4-(2-oxocyclopentan-1-yl-methyl)phenyl]-propionate [INN: LOXOPROFEN], 2(R)-[4-(3-methyl-2-thienyl)phenyl]propionic acid [Research Code: M-5010], N-(2,3-xylyl)anthranilic acid [INN: MEFENAMIC ACID], 4-hydroxy-2-methyl-N-(5-methyl-2-thiazolyl)-2H-1,2-benzothiazine-3-carboxamide 1,1-dioxide [INN: MELOXICAM], 5-aminosalicylic acid [INN: MESALAZINE], (2,2-dimethyl-6-(4-chlorophenyl)-7-phenyl-2,3-dihydro-1H-pyrrolizin-5-yl)-acetic acid [Research Code: ML-3000], 3,4-bis(4-methoxyphenyl)-5-isoxazoleacetic acid [INN: MOFEZOLAC], 4-(6-methoxy-2-naphthyl)-2-butanone [INN: NABUMETONE], (plus)-6-methoxy-alpha-methyl-2-naphthalineacetic acid [INN: NAPROXEN], 2-[3-(trifluoromethyl)anilino]nicotinic acid [INN: NIFLUMIC ACID], 5,5'-azodisalicylic acid [INN: OLSALAZINE], alpha-methyl-4-[(2-oxocyclohexylidene)methyl]benzene acetic acid [INN: PELUBIPROFEN], 2-(p-isobutylphenyl)propionic acid 2-pyridyl-methyl ester [INN: PIMEPROFEN], 4-(p-chlorophenyl)-1-(p-fluorophenyl)pyrazole-3-acetic acid [INN: PIRAZOLAC], 4-hydroxy-2-methyl-N-2-pyridyl-2H-1,2-benzothiadiazin-3-carboxamide 1,1-dioxide [INN: PIROXICAM], 3-chloro-4-(3-pyrrolin-1-yl)hydratropic acid [INN: PIRPROFEN], 2-[5H-(1)benzopyrano]2,3-b]pyridin-7-yl]propionic acid [INN: PRANOPROFEN], 2,6-di-tert-butyl-4-(2'-thenoyl)phenol [INN: PRIFELONE], alpha-cyano-1-methyl-beta-oxopyrrole-2-propionanilide [INN: PRINOMIDE], 3-[4-(2-hydroxyethyl)-1-piperazinyl]-propyl-D,L-4-benzamido-N,N-dipropylglutaramat 1-(p-chlorobenzoyl)-5-methoxy-2-methylindole-3-acetate (ester) [INN: PROGLUMETACIN], 7-methyl-1-(1-methylethyl)-4-phenyl-2(1H)quinazolinone [INN: PROQUAZONE], 7-methoxy-alpha,10-dimethylphenothiazine-2-acetic acid [INN: PROTIZINIC] ACID], 2-[[2-(p-chlorophenyl)-4-methyl-5-oxazolyl]methoxy]-2-methylpropionic acid [INN: ROMAZARIT], o-hydroxybenzamide [SALICYLAMIDE], 2-hydroxybenzoic acid [SALICYLIC ACID], N-acetyl-L-cysteine salicylate (ester), acetate (ester) [INN: SALMISTEINE], N-acetyl-L-cysteine salicylate (ester) [INN: SALNACEDIN], 2-hydroxybenzoic acid 2-carboxyphenyl ester [INN: SALSALATE], 4-[1-(2-fluorobiphenyl-4-yl)ethyl]-N-methylthiazole-2-amine [Research Code: SM-8849], (Z)-5-fluoro-2-methyl-1-[p-(methylsulfinyl)benzylidene]indene-3-acetic acid [INN: SULINDAC], p-2-thenoylhydratropic acid [INN: SUPROFEN] 2-(4-(3-methyl-2-butenyl)phenyl)propionic acid [Research Code: TA-60], phthalidyl 2-(alpha,alpha,alpha-trifluoro-m-toluidino)nicotinate [INN: TALNIFLUMATE], (Z)-5-chloro-3-(2-thenoyl)-2-oxoindole-1-carboxamide [INN: TENIDAP], 2-thiophenecarboxylic acid, ester with salicylic acid [INN: TENOSAL], 4-hydroxy-2-methyl-N-2-pyridyl-2H-thieno[2,3-e]-1,2-thiazine-3-carboxamide [INN: TENOXICAM], 5-(4-chlorophenyl)-N-hydroxy-1-(4-methoxyphenyl)-N-methyl-1H-pyrazole-3-propionamide [INN: TEPOXALIN], alpha-(5-benzoyl-2-thienyl)propionic acid [INN: TIAPROFENIC ACID], 5-chloro-3-[4-(2-hydroxyethyl)-1-piperazinyl]carbonylmethyl-2-benzo-thiazolin one [INN: TIARAMIDE], 2-(2-methyl-5H-[1]benzopyrano[2,3-b]pyridin-7-yl)-propionic acid N,N-dimethylcarbamoylmethyl ester [INN: TILNOPROFEN ARBAMEL], 1-Cyclohexyl-2-(2-methyl-4-quinolyl)-3-(2-thiazolyl)guanidine [INN: TIMEGADINE], 2-amino-6-benzyl-4,5,6,7-tetrahydrothieno[2,3-c]pyridine [INN: TINORIDINE], N-(3-chloro-o-tolyl) anthranilic acid [INN: TOLFENAMIC ACID], 1-methyl-5-(4-methylbenzoyl)-1H-pyrrole-2-acetic acid [INN: TOLMETIN], hydroxybis[alpha-methyl-4-(2-methylpropyl)benzene acetato-O]-aluminium [Research Code: U-18573-G], N-(3-trifluoromethylphenyl)-anthranilic acid n-butyl ester [INN: UFENAMATE], 2-[4-[3-(hydroxyimino)cyclohexyl]phenyl]propionic acid [INN: XIMOPROFEN], 2-(10,11-dihydro-10-oxo-dibenz[b,f]thiepin-2-yl-propionic acid [INN: ZALTOPROFEN] and 2-[4-(2-thiazolyloxy)phenyl]-propionic acid [INN: ZOLIPROFEN].

Preferred conventional NSAIDs which are selected from the above-defined group of conventional NSAIDs are 2-(acetyloxy)benzoic acid [ACETYLSALICYLIC ACID], 2-[(2,6-dichlorophenyl)amino]-benzeneacetic acid [INN: DICLOFENAC], alpha-p-isobutylphenylpropionic acid [INN: IBUPROFEN],], 1-(4-chlorobenzoyl)-5-methoxy-2-methyl-1H-indole-3-acetic acid [INN: INDOMETACIN], (plus)-6-meth-oxy-alpha-methyl-2-naphthalineacetic acid [INN: NAPROXEN] and 4-hydroxy-2-methyl-N-2-pyridyl-2H-1,2-benzothiadiazin-3-carboxamide 1,1-dioxide [INN: PIROXICAM].

An particularly preferred conventional NSAID is 2-[(2,6-dichlorophenyl)amino]benzeneacetic acid [INN: DICLOFENAC].

In the context of the present invention, unless otherwise stated, a pharmaceutically acceptable derivative of an active ingredient means a pharmaceutically acceptable salt or solvate (e.g. hydrate), a pharmaceutically acceptable solvate of such salt, a pharmaceutically acceptable N-oxide or a pharmaceutically acceptable salt or solvate of the latter.

Suitable pharmacologically tolerable salts here are on the one hand in particular water-soluble and water-insoluble acid addition salts with acids such as, for example, hydrochloric acid, hydrobromic acid, phosphoric acid, nitric acid, sulfuric acid, acetic acid, citric acid, D-gluconic acid, benzoic acid, 2-(4-hydroxybenzoyl)-benzoic acid, butyric acid, sulfosalicylic acid, maleic acid, lauric acid, malic acid, fumaric acid, succinic acid, oxalic acid, tartaric acid, embonic acid, stearic acid, toluenesulfonic acid, methanesulfonic acid or 1-hydroxy-2-naphthoic acid, the acids being employed in salt preparation—depending on whether it is a mono- or polybasic acid and depending on which salt is desired—in an equimolar quantitative ratio or one differing therefrom. Furthermore, the active compounds mentioned can also be present as pure enantiomers or as enantiomer mixtures in any mixing ratio.

On the other hand, salts with bases are also suitable. Examples of salts with bases which may be mentioned are alkali metal (lithium, sodium, potassium) or calcium, aluminum, magnesium, titanium, ammonium, meglumine or guanidinium salts, where here too the bases are employed in salt preparation in an equimolar quantitative ratio or one differing therefrom.

Certain of the active ingredients used in the present invention are capable of existing in stereoisomeric forms. The invention encompasses all stereoisomers of the active ingredients and mixtures thereof including racemates. Tautomers and mixtures thereof of the active ingredients are also part of the present invention.

In accordance with the present invention, there is provided in a first aspect a pharmaceutical composition comprising, in admixture, a first active ingredient which is a PDE4-inhibitor selected from CDC-998, SH-636, D-4396, IC-485, CC-1088 and 3,5-dichloro-4-[8-methoxy-2-(trifluoromethyl)quinoline-5-ylcarboxamido]pyridine-1-oxide [Research Code: SCH351591], 3-[3-(cyclopentyloxy)-4-methoxybenzyl]-6-(ethylamino)-8-isopropyl-3H-purine [Research-Code: V-11294A], N-[9-methyl-4-oxo-1-phenyl-3,4,6,7-tetrahydropyrrolo[3,2,1-jk][1,4]benzo-diazepin-3(R)-yl]pyridine-4-carboxamide [Research-Code: CI-1018, N-(3,5-dichloro-4-pyridinyl)-2-[1-(4-fluorobenzyl)-5-hydroxy-1H-indol-3-yl]-2-oxoacetamide [Research-Code: AWD-12-281], N-(3,5-dichloropyridin-4-yl)-2-[5-fluoro-1-(4-fluorobenzyl)-1H-indol-3-yl]-2-oxoacetamide [Research-Code: AWD-12-343], 8-Amino-1,3-bis(cyclopropylmethyl)xanthine [INN: CIPAMFYLLINE], Tetrahydro-5-[4-methoxy-3-[(S,2S,4R)-2-norbornyloxy]phenyl]-2(1H)-pyrimidone [INN: ATIZORAM], β-[3-(Cyclopentyloxy)-4-methoxyphenyl]-1,3-dihydro-1,3-dioxo-2H-isoindole-2-propanamide [Research-Code: CDC-801], Methanesulfonic acid 2-(2,4-dichlorophenyl-carbonyl)-3-ureidobenzo-furan-6-yl ester [INN: LIRIMILAST], N-(3,5-dichloropyrid-4-yl)-3-cyclopentyl-oxy-4-methoxybenzamide [INN: PICLAMILAST], cis-[4-Cyano-4-(3-cyclopentyloxy-4-methoxyphenyl)-cyclohexane-1-carboxylic acid [INN: CILOMILAST], 3-Cyclopropylmethoxy-4-difluoromethoxy-N-(3,5-dichloropyrid-4-yl)-benzamide [INN: ROFLUMILAST] and their pharmaceutically acceptable derivatives, and a second active ingredient which is a conventional NSAID selected from glycolic acid [o-(2,6-dichloroanilino)phenyl]acetate(ester) [INN: ACECLOFENAC]; 1-(4-chlorobenzoyl)-5-methoxy-2-meth-yl-1H-indole-3-acetic acid carboxymethyl ester [INN: ACEMETACIN]; 2-(acetyloxy)benzoic acid [ACETYLSALICYLIC ACID], 2-methoxyphenyl-alpha-methyl-4-(isobutyl)phenylacetate [Research Code: AF-2259], (4-allyloxy-3-chlorophenyl)acetic acid [INN: ALCLOFENAC], p-[(2-methylallyl)amino]hydratropic acid [INN: ALMINOPROFEN], 2-amino-3-benzoylphenylacetic acid [INN: AMFENAC], (plus/minus)-4-(1-hydroxyethoxy)-2-methyl-N-2-pyridyl-2H-1,2-benzothiazine-3-carboxamide ethylcarbonate (ester), 1,1-dioxide [INN: AMPIROXICAM], 2-methoxyphenyl-1-methyl-5-(p-methylbenzoyl)pyrrol-2-acetamido-acetate [INN: AMTOLMETINGUACIL], (plus/minus)-2,3-dihydro-5-(4-methoxybenzoyl)-1H pyrrolizine-1-carboxylic acid [INN: ANIROLAC], 2-[4-(alpha,alpha,alpha-trifluoro-m-tolyl)-1-piperazinyl]-ethyl-N-(7-trifluoromethyl-4-quinolyl)anthranilate [INN: ANTRAFENINE], 5-(dimethylamino)-9-methyl-2-propyl-1H-pyrazolo[1,2-a][1,2,4]benzo-triazine-1,3(2H)-dione [INN: AZAPROPAZONE], 4-acetamido-phenyl salicylate acetate [INN: BENORILATE], 2-(8-methyl-10,11-dihydro-11-oxodibenz[b,f]oxepin-2-yl)propionic acid [INN: BERMOPROFEN], 2-[(1-benzyl-1H-indazol-3-yl)methoxy]-2-methylpropionic acid [INN: BINDARIT], [2-amino-3-(p-bromobenzoyl)phenyl]acetic acid [INN: BROMFENAC], 3-(3-chloro-4-cyclohexylbenzoyl)propionic acid [INN: BUCLOXIC ACID], 5-butyl-1-cyclohexylbarbituric acid [INN: BUCOLOM], 4-butoxy-N-hydroxybenzeneacetamide [INN: BUFEXAMAC], butylmalonic acid mono(1,2-diphenylhydrazide) [INN: BUMADIZONE], alpha-ethyl-4-(2-methylpropyl)benzeneacetic acid [INN: BUTIBUFEN], 2-(4-biphenylyl)butyric acid, trans-4-phenylcyclohexylamine salt (1:1) [INN: BUTIXIRATE], 2-(acetyloxy)-benzoic acid, calcium salt, compound with urea (1:1) [INN: CARBASALATE CALCIUM], (plus/minus)-6-chloro-alpha-methylcarbazole-2-acetic acid [INN: CARPROFEN], 1-cinnamoyl-5-methoxy-2-methylindole-3-acetic acid [INN: CINMETACIN], N-(2-pyridyl)-2-methyl-4-cinnamoyloxy-2H-1,2-benzothiazine-3-carboxamide-1,1-dioxide [INN: CINNOXICAM], 6-chloro-5-cyclohexyl-1-indancarboxylic acid [INN: CLIDANAC], 2-[4-(p-chlorophenyl)benzyloxy]-2-methylpropionic acid [INN: CLOBUZARIT], 5-methoxy-2-methyl-3-indolylacetohydroxamic acid [INN: DEBOXAMET], (S)-(+)-p-isobutylhydratropic acid [INN: DEXIBUPROFEN], (+)-(S)-m-benzoylhydratropic acid [INN: DEXKETOPROFEN], 2-[(2,6-dichlorophenyl)amino]benzeneacetic acid [INN: DICLOFENAC], 2',4'-Difluoro-4-hydroxy-3-biphenylcarboxylic acid [INN: DIFLUNISAL], 4-(2,6-dichloroanilino)-3-thiopheneacetic acid [INN: ELTENAC], N-beta-phenethyl-anthranilic acid [INN: ENFENAMIC ACID] salicylic acid acetate, ester with beta-hydroxy p-acetophenetidide [INN: ETERSALATE], 1,8-diethyl-1,3,4,9-tetrahydropyrano[3,4-b]indole-1-acetic acid [INN: ETODOLAC], 2-[[3-(trifluoromethyl)phenyl]amino]benzoic acid 2-(2-hydroxyethoxy)-ethyl ester [INN: ETOFENAMATE], p-chlorobenzoic acid, ester with 4-butyl-4-(hydroxymethyl)-1,2-diphenyl-3,5-pyrazolidinedione [INN: FECLOBUZONE], 4-biphenylacetic acid [INN: FELBINAC], 3-(4-biphenylylcarbonyl)propionic acid [INN: FENBUFEN], [o-(2,4-dichlorophenoxy)phenyl]acetic acid [INN: FENCLOFENAC], (plus/minus)-m-phenoxyhydratropic acid [INN: FENOPROFEN], 4-(p-chlorophenyl)-2-phenyl-5-thiazoleacetic acid [INN: FENTIAZAC], (plus/minus)-alpha-[[(2-hydroxy-1,1-dimethylethyl)amino]methyl]-benzyl alcohol [INN: FEPRADINOL], 4-(2',4'-difluorobiphenylyl)-4-oxo-2-methylbutanoic acid [INN: FLOBUFEN], N-(alpha,alpha,alpha-trifluoro-m-tolyl)anthranilic acid [INN: FLUFENAMIC ACID], (plus)-2-(p-fluorophenyl)-alpha-methyl-5-benzoxazoleacetic acid [INN: FLUNOXAPROFEN], 2-fluoro-alpha-methyl-4-biphenylacetic acid [INN: FLURBIPROFEN], (plus/minus)-2-(2-fluoro-4-biphenylyl)propionic acid 1 (acetoxy)ethyl ester [INN: FLURBIPROFEN AXETIL], 2-ethyl-2,3-dihydro-5-benzofuranacetic acid [INN: FUROFENAC], 2-[4-(2'-furoyl)phenyl]propionic acid [INN: FURPROFEN], 2-[2-[1-(p-chlorobenzoyl)-5-methoxy-2-methylindol-3-yl]acetamido]-2-deoxy-D-glucose [INN: GLUCAMETACIN], 2-(2-fluorobiphenyl-4-yl)propionic acid 4-nitrooxybutylester [Research Code: HCT-1026], (p-isobutylphenyl)acetic acid [INN: IBUFENAC], alpha-p-isobutylphenylpropionic acid [INN: IBUPROFEN], methyl 4-(3-thienyl)phenyl-alpha-methylacetate [Research Code: IDPH-8261], (plus/minus)-2-[p-(1-oxo-2-isoindolinyl)phenyl]butyric acid [INN: INDOBUFEN], 1-(4-chlorobenzoyl)-5-methoxy-2-methyl-1H-indole-3-acetic acid [INN: INDOMETACIN], 1-(4-chlorobenzoyl)-5-methoxy-2-methyl-1H-indole-3-acetic acid, 3,7,11-trimethyl-2,6,10-dodecatrienyl ester [INN: INDOMETACIN. FARNESIL], p-(1-oxo-2-isoindolinyl)hydratropic acid [INN: INDOPROFEN], 2-(10-methoxy-4H-benzo[4,5]cyclohepta[1,2-b]thiophen-4-ylidene)-acetic acid [Research Code: IX-207-887], m-benzoyl-hydratropic acid [INN: KETOPROFEN], (DL)-5-benzoyl-3H-1,2-dihydropyrrolo[1,2-a]pyrrole-1-carboxylic acid [INN: KETOROLAC], 2,3-dihydro-5-hydroxy-6-[2-(hydroxymethyl)cinnamyl] benzofuran [Research Code: L-651896], N-(2-carboxyphenyl)-4-chloroanthranilic acid [INN: LOBENZARIT], 3-(p-chlorophenyl)-1-phenylpyrazole-4-acetic acid [INN:

LONAZOLAC], 6-chloro-4-hydroxy-2-methyl-N-2-pyridyl-2H-thieno[2,3-e]-1,2-thiazine-3-carboxamide 1,1-dioxide [INN: LORNOXICAM], 2-[4-(2-oxocyclopentan-1-ylmethyl)phenyl]-propionate [INN: LOXOPROFEN], 2(R)-[4-(3-methyl-2-thienyl)phenyl]propionic acid [Research Code: M-5010], N-(2,3-xylyl)anthranilic acid [INN: MEFENAMIC ACID], 4-hydroxy-2-methyl-N-(5-methyl-2-thiazolyl)-2H-1,2-benzothiazine-3-carboxamide 1,1-dioxide [INN: MELOXICAM], 5-aminosalicylic acid [INN: MESALAZINE], (2,2-dimethyl-6-(4-chlorophenyl)-7-phenyl-2,3-dihydro-1H-pyrrolizin-5-yl)-acetic acid [Research Code: ML-3000], 3,4-bis(4-methoxyphenyl)-5-isoxazoleacetic acid [INN: MOFEZOLAC], 4-(6-methoxy-2-naphthyl)-2-butanone [INN: NABUMETONE], (plus)-6-methoxy-alpha-methyl-2-naphthalineacetic acid [INN: NAPROXEN], 2-[3-(trifluoromethyl)anilino]nicotinic acid [INN: NIFLUMIC ACID], 5,5'-azodisalicylic acid [INN: OLSALAZINE], alpha-methyl-4-[(2-oxocyclohexylidene)methyl]benzene acetic acid [INN: PELUBIPROFEN], 2-(p-isobutylphenyl)propionic acid 2-pyridyl-methyl ester [INN: PIMEPROFEN], 4-(p-chlorophenyl)-1-(p-fluorophenyl)pyrazole-3-acetic acid [INN: PIRAZOLAC], 4-hydroxy-2'-methyl-N-2-pyridyl-2H-1,2-benzothiadiazin-3-carboxamide 1,1-dioxide [INN: PIROXICAM], 3-chloro-4-(3-pyrrolin-1-yl)hydratropic acid [INN: PIRPROFEN], 2-[5H-(1)benzopyrano]2,3-b]pyridin-7-yl]propionic acid [INN: PRANOPROFEN], 2,6-di-tert-butyl-4-(2'-thenoyl)phenol [INN: PRIFELONE], alpha-cyano-1-methyl-beta-oxopyrrole-2-propionanilide [INN: PRINOMIDE], 3-[4-(2-hydroxyethyl)-1-piperazinyl]-propyl-D,L-4-benzamido-N,N-dipropylglutaramat 1-(p-chlorobenzoyl)-5-methoxy-2-methylindole-3-acetate (ester) [INN: PROGLUMETACIN], 7-methyl-1-(1-methylethyl)-4-phenyl-2(1H)quinazolinone [INN: PROQUAZONE], 7-methoxy-alpha,10-dimethylphenothiazine-2-acetic acid [INN: PROTIZINIC ACID], 2-[[2-(p-chlorophenyl)-4-methyl-5-oxazolyl]methoxy]-2-methylpropionic acid [INN: ROMAZARIT], o-hydroxybenzamide [SALICYLAMIDE], 2-hydroxy-1-benzoic acid [SALICYLIC ACID], N-acetyl-L-cysteine salicylate (ester), acetate (ester) [INN: SALMISTEINE], N-acetyl-L-cysteine salicylate (ester) [INN: SALNACEDIN], 2-hydroxybenzoic acid 2-carboxyphenyl ester [INN: SALSALATE], 4-[1-(2-fluorobiphenyl-4-yl)ethyl]-N-methylthiazole-2-amine [Research Code: SM-8849], (Z)-5-fluoro-2-methyl-1-[p-(methylsulfinyl)benzylidene]indene-3-acetic acid [INN: SULINDAC], p-2-thenoylhydratropic acid [INN: SUPROFEN] 2-(4-(3-methyl-2-butenyl)phenyl)-propionic acid [Research Code: TA-60], phthalidyl 2-(alpha,alpha,alpha-trifluoro-m-toluidino)nicotinate [INN: TALNIFLUMATE], (Z)-5-chloro-3-(2-thenoyl)-2-oxoindole-1-carboxamide [INN: TENIDAP], 2-thiophenecarboxylic acid, ester with salicylic acid [INN: TENOSAL], 4-hydroxy-2-methyl-N-2-pyridyl-2H-thieno[2,3-e]-1,2-thiazine-3-carboxamide [INN: TENOXICAM], 5-(4-chlorophenyl)-N-hydroxy-1-(4-methoxyphenyl)-N-methyl-1H-pyrazole-3-propionamide [INN: TEPOXALIN], alpha-(5-benzoyl-2-thienyl)propionic acid [INN: TIAPROFENIC ACID], 5-chloro-3-[4-(2-hydroxyethyl)-1-piperazinyl]carbonyl-methyl-2-benzo-thiazolin one [INN: TIARAMIDE], 2-(2-methyl-5H-[1]benzopyrano[2,3-b]pyridin-7-yl)-propionic acid N,N-dimethylcarbamoylmethyl ester [INN: TILNOPROFEN ARBAMEL], 1-Cyclohexyl-2-(2-methyl-4-quinolyl)-3-(2-thiazolyl)guanidine [INN: TIMEGADINE], 2-amino-6-benzyl-4,5,6,7-tetrahydrothieno[2,3-c]pyridine [INN: TINORIDINE], N-(3-chloro-o-tolyl)anthranilic acid [INN: TOLFENAMIC ACID], 1-methyl-5-(4-methylbenzoyl)-1H-pyrrole-2-acetic acid [INN: TOLMETIN], hydroxybis[alpha-methyl-4-(2-methylpropyl)benzene acetato-O]-aluminium [Research Code: U-18573-G], N-(3-trifluoromethylphenyl)-anthranilic acid n-butyl ester [INN: UFENAMATE], 2-[4-[3-(hydroxyimino)cyclohexyl]phenyl]propionic acid [INN: XIMOPROFEN], 2-(10,11-dihydro-10-oxo-dibenz[b,f]thiepin-2-yl-propionic acid [INN: ZALTOPROFEN], 2-[4-(2-thiazolyloxy)phenyl]-propionic acid [INN: ZOLIPROFEN] and their pharmaceutically acceptable derivatives.

In a second aspect—which is an embodiment of the first aspect—there is provided a pharmaceutical composition comprising, in admixture, a first active ingredient which is a PDE4-inhibitor selected from cis-[4-Cyano-4-(3-cyclopentyloxy-4-methoxyphenyl)cyclohexane-1-carboxylic acid [INN: CILOMILAST], 3-Cyclopropylmethoxy-4-difluoromethoxy-N-(3,5-dichloropyrid-4-yl)-benzamide [INN: ROFLUMILAST] and their pharmaceutically acceptable derivatives, and a second active ingredient which is a conventional NSAID selected from 2-(acetyloxy)benzoic acid [ACETYLSALICYLIC ACID], 2-[(2,6-di-chlorophenyl)amino]benzeneacetic acid [INN: DICLOFENAC], alpha-p-isobutylphenylpropionic acid [INN: IBUPROFEN],], 1-(4-chlorobenzoyl)-5-methoxy-2-methyl-1H-indole-3-acetic acid [INN: INDOMETACIN], (plus)-6-methoxy-alpha-methyl-2-naphthalineacetic acid [INN: NAPROXEN], 4-hydroxy-2-methyl-N-2-pyridyl-2H-1,2-benzothiadiazin-3-carboxamide 1,1-dioxide [INN: PIROXICAM] and their pharmaceutically acceptable derivatives.

In a third aspect—which is another embodiment of the first aspect—there is provided a pharmaceutical composition comprising, in admixture, a first active ingredient which selected from 3-Cyclopropylmethoxy-4-difluoromethoxy-N-(3,5-dichloropyrid-4-yl)-benzamide [INN: ROFLUMILAST] and its Pharmaceutically acceptable derivatives, and a second active ingredient which is selected from 2-[(2,6-dichlorophenyl)amino]benzeneacetic acid [INN: DICLOFENAC] and its pharmaceutically acceptable derivatives.

In a forth aspect the invention provides a pharmaceutical product comprising, in combination, a preparation of a first active ingredient which is a PDE4-inhibitor selected from CDC-998, SH-636, D-4396, IC-485, CC-1088 and 3,5-dichloro-4-[8-methoxy-2-(trifluoromethyl)quinoline-5-yl-carboxamido]pyridine-1-oxide [Research Code: SCH351591], 3-[3-(cyclopentyloxy)-4-methoxybenzyl]-6-(ethylamino)-8-isopropyl-3H-purine [Research-Code: V-11294A], N-[9-methyl-4-oxo-1-phenyl-3,4,6,7-tetrahydropyrrolo[3,2,1-jk][1,4]benzo-diazepin-3(R)-yl]pyridine-4-carboxamide [Research-Code: CI-1018, N-(3,5-dichloro-4-pyridinyl)-2-[1-(4-fluorobenzyl)-5-hydroxy-1H-indol-3-yl]-2-oxoacetamide [Research-Code: AWD-12-281], N-(3,5-dichloropyridin-4-yl)-2-[5-fluoro-1-(4-fluorobenzyl)-1H-indol-3-yl]-2-oxoacetamide [Research-Code: AWD-12-343], 8-Amino-1,3-bis(cyclopropylmethyl)xanthine [INN: CIPAMFYLLINE], Tetrahydro-5-[4-methoxy-3-[(1S,2S,4R)-2-norbornyloxy]phenyl]-2(1H)-pyrimidone [INN: ATIZORAM], β-[3-(Cyclopentyloxy)-4-methoxyphenyl]-1,3-dihydro-1,3-dioxo-2H-isoindole-2-propanamide [Research-Code: CDC-801], Methanesulfonic acid 2-(2,4-dichlorophenylcarbonyl)-3-ureidobenzo-furan-6-yl ester [INN: LIRIMILAST], N-(3,5-dichloropyrid-4-yl)-3-cyclopentyloxy-4-methoxybenzamide [INN: PICLAMILAST], cis-[4-Cyano-4-(3-cyclopentyloxy-4-methoxyphenyl)cyclohexane-1-carboxylic acid [INN: CILOMILAST], 3-Cyclopropylmethoxy-4-difluoromethoxy-N-(3,5-dichloropyrid-4-yl)-benzamide [INN: ROFLUMILAST] and their pharmaceutically acceptable derivatives, and a preparation of a second active ingredient which is a conventional NSAID selected from glycolic acid [o-(2,6-dichloroanilino)phenyl] acetate(ester) [INN: ACECLOFENAC]; 1-(4-chlorobenzoyl)-5-methoxy-2-methyl-1H-indole-3-acetic acid carboxymethyl ester [INN: ACEMETACIN]; 2-(acetyloxy)benzoic acid [ACETYLSALICYLIC ACID], 2-methoxyphenyl-alpha-methyl-4-(isobutyl)phenylacetate [Research Code: AF-2259], (4-allyloxy-3-chlorophenyl)acetic acid [INN: ALCLOFENAC], p-[(2-methylallyl)amino] hydratropic acid [INN: ALMINOPROFEN], 2-amino-3-benzoylphenylacetic acid [INN: AMFENAC], (plus/minus)-4-(1-hydroxyethoxy)-2-methyl-N-2-pyridyl-2H-1,2-benzothiazine-3-carboxamide ethylcarbonate (ester), 1,1-dioxide [INN: AMPIROXICAM], 2-methoxyphenyl-1-methyl-5-(p-methylbenzoyl)pyrrol-2-acetamido-acetate [INN: AMTOLMETINGUACIL], (plus/minus)-2,3-dihydro-5-(4-methoxybenzoyl)-1H pyrrolizine-1-carboxylic acid [INN: ANIROLAC], 2-[4-(alpha,alpha,alpha-trifluoro-m-tolyl)-1-piperazinyl]ethyl-N-(7-trifluoromethyl-4-quinolyl) anthranilate [INN: ANTRAFENINE], 5-(dimethylamino)-9-methyl-2-propyl-1H-pyrazolo[1,2-a][1,2,4]benzo-triazine-1,3(2H)-dione [INN: AZAPROPAZONE], 4-acetamidophenyl salicylate acetate [INN: BENORILATE], 2-(8-methyl-10,11-dihydro-11-oxodibenz[b,f]oxepin-2-yl) propionic acid [INN: BERMOPROFEN], 2-[(1-benzyl-1H-indazol-3-yl)methoxy]-2-methylpropionic acid [INN: BINDARIT], [2-amino-3-(p-bromobenzoyl)phenyl]acetic acid [INN: BROMFENAC], 3-(3-chloro-4-cyclohex-ylbenzoyl) propionic acid [INN: BUCLOXIC ACID], 5-butyl-1-cyclohexylbarbituric acid [INN: BUCOLOM], 4-butoxy-N-hydroxybenzeneacetamide [INN: BUFEXAMAC], butylmalonic acid mono(1,2-diphenylhydrazide) [INN: BUMADIZONE], alpha-ethyl-4-(2-methylpropyl)benzeneacetic acid [INN: BUTIBUFEN], 2-(4-biphenylyl)butyric acid, trans-4-phenylcyclohexylamine salt (1:1) [INN: BUTIXIRATE], 2-(acetyloxy)-benzoic acid, calcium salt, compound with urea (1:1) [INN: CARBASALATE CALCIUM], (plus/minus)-6-chloro-alpha-methylcarbazole-2-acetic acid [INN: CARPROFEN], 1-cinnamoyl-5-methoxy-2-methylindole-3-acetic acid [INN: CINMETACIN], N-(2-pyridyl)-2-methyl-4-cinnamoyloxy-2H-1,2-benzothiazine-3-carboxamide-1,1-dioxide [INN: CINNOXICAM], 6-chloro-5-cyclohexyl-1-indancarboxylic acid [INN: CLIDANAC], 2-[4-(p-chlorophenyl)benzyloxy]-2-methylpropionic acid [INN: CLOBUZARIT], 5-methoxy-2-methyl-3-indolylacetohydroxamic acid [INN: DEBOXAMET], (S)-(+)-p-isobutylhydratropic acid [INN: DEXIBUPROFEN], (+)-(S)-m-benzoylhydratropic acid [INN: DEXKETOPROFEN], 2-[(2,6-dichlorophenyl)amino]benzeneacetic acid [INN: DICLOFENAC], 2',4'-Difluoro-4-hydroxy-3-biphenylcarboxylic acid-[INN: DIFLUNISAL], 4-(2,6-dichloroanilino)-3-thiopheneacetic acid [INN: ELTENAC], N-beta-phenethyl-anthranilic acid [INN: ENFENAMIC ACID] salicylic acid acetate, ester with beta-hydroxy p-acetophenetidide [INN: ETERSALATE], 1,8-diethyl-1,3,4,9-tetrahydropyrano[3,4-b]indole-1-acetic acid [INN: ETODOLAC], 2-[[3-(trifluoromethyl)phenyl]amino] benzoic acid 2-(2-hydroxy-ethoxy)-ethyl ester [INN: ETOFENAMATE], p-chlorobenzoic acid, ester with 4-butyl-4-(hydroxymethyl)-1,2-diphenyl-3,5-pyrazolidinedione [INN: FECLOBUZONE], 4-biphenylacetic acid [INN: FELBINAC], 3-(4-biphenylylcarbonyl)propionic acid [INN: FENBUFEN], [o-(2,4-dichlorophenoxy)phenyl]acetic acid [INN: FENCLOFENAC], (plus/minus)-m-phenoxyhydratropic acid [INN: FENOPROFEN], 4-(p-chloro-phenyl)-2-phenyl-5-thiazoleacetic acid [INN: FENTIAZAC], (plus/minus)-alpha-[[(2-hydroxy-1,1-dimethylethyl)amino]methyl]-benzyl alcohol [INN: FEPRADINOL], 4-(2',4'-difluorobiphenylyl)-4-oxo-2-methylbutanoic acid [INN: FLOBUFEN], N-(alpha,alpha,alpha-trifluoro-m-tolyl)anthranilic acid [INN: FLUFENAMIC ACID], (plus)-2-(p-fluorophenyl)-alpha-methyl-5-benzoxazoleacetic acid [INN: FLUNOXAPROFEN], 2-fluoro-alpha-methyl-4-biphenylacetic acid [INN: FLURBIPROFEN], (plus/minus)-2-(2-fluoro-4-biphenylyl)propionic acid 1 (acetoxy)ethyl ester [INN: FLURBIPROFEN AXETIL], 2-ethyl-2,3-dihydro-5-benzofuranacetic acid [INN: FUROFENAC], 2-[4-(2'-furoyl)phenyl]propionic acid [INN: FURPROFEN], 2-[2-[1-(p-chlorobenzoyl)-5-methoxy-2-methylindol-3-yl] acetamido]-2-deoxy-D-glucose [INN: GLUCAMETACIN], 2-(2-fluorobiphenyl-4-yl)propionic acid 4-nitrooxybutylester [Research Code: HCT-1026], (p-isobutylphenyl)acetic acid [INN: IBUFENAC], alpha-p-isobutylphenylpropionic acid [INN: IBUPROFEN], methyl 4-(3-thienyl)phenyl-alpha-methylacetate [Research Code: IDPH-8261], (plus/minus)-2-[p-(1-oxo-2-isoindolinyl)phenyl]butyric acid [INN: INDOBUFEN], 1-(4-chlorobenzoyl)-5-methoxy-2-methyl-1H-indole-3-acetic acid [INN: INDOMETACIN], 1-(4-chlorobenzoyl)-5-methoxy-2-methyl-1H-indole-3-acetic acid, 3,7,11-trimethyl-2,6,10-dodecatrienyl ester [INN: INDOMETACIN FARNESIL], p-(1-oxo-2-isoindolinyl)hydratropic acid [INN: INDOPROFEN], 2-(10-methoxy-4H-benzo[4,5]-cyclohepta[1,2-b]thiophen-4-ylidene)-acetic acid [Research Code: IX-207-887], m-benzoylhydratropic acid [INN: KETOPROFEN], (DL)-5-benzoyl-3H-1,2-dihydropyrrolo[1,2-a]pyrrole-1-carboxylic acid [INN: KETOROLAC], 2,3-dihydro-5-hydroxy-6-[2-(hydroxymethyl)cinnamyl]benzofuran [Research Code: L-651896], N-(2-carboxyphenyl)-4-chloroanthranilic acid [INN: LOBENZARIT], 3-(p-chlorophenyl)-1-phenylpyrazole-4-acetic acid [INN: LONAZOLAC], 6-chloro-4-hydroxy-2-methyl-N-2-pyridyl-2H-thieno[2,3-e]-1,2-thiazine-3-carboxamide 1,1-dioxide [INN: LORNOXICAM], 2-[4-(2-oxocyclopentan-1-yl-methyl)phenyl]-propionate [INN: LOXOPROFEN], 2(R)-[4-(3-methyl-2-thienyl)phenyl]propionic acid [Research Code: M-5010], N-(2,3-xylyl)anthranilic acid [INN: MEFENAMIC ACID], 4-hydroxy-2-methyl-N-(5-methyl-2-thiazolyl)-2H-1,2-benzothiazine-3-carboxamide 1,1-dioxide [INN: MELOXICAM], 5-aminosalicylic acid [INN: MESALAZINE], (2,2-dimethyl-6-(4-chlorophenyl)-7-phenyl-2,3-dihydro-1H-pyrrolizin-5-yl)-acetic acid [Research Code: ML-3000], 3,4-bis (4-n-methoxyphenyl)-5-isoxazoleacetic acid [INN: MOFEZOLAC], 4-(6-methoxy-2-naphthyl)-2-butanone [INN: NABUMETONE], (plus)-6-methoxy-alpha-methyl-2-naphthalineacetic acid [INN: NAPROXEN], 2-[3-(trifluoromethyl)anilino]nicotinic acid [INN: NIFLUMIC ACID], 5,5'-azodisalicylic acid [INN: OLSALAZINE], alpha-methyl-4-[(2-oxocyclohexylidene)methyl]benzene acetic acid [INN: PELUBIPROFEN], 2-(p-isobutylphenyl)propionic acid 2-pyridyl-methyl ester [INN: PIMEPROFEN], 4-(p-chlorophenyl)-1-(p-fluorophenyl)pyrazole-3-acetic acid [INN: PIRAZOLAC], 4-hydroxy-2-methyl-N-2-pyridyl-2H-1,2-benzothiadiazin-3-carboxamide 1,1-dioxide [INN: PIROXICAM], 3-chloro-4-(3-pyrrolin-1-yl)hydratropic acid [INN: PIRPROFEN], 2-[5H-(1)benzopyrano]2,3-b]pyridin-7-yl]propionic acid [INN: PRANOPROFEN], 2,6-di-tert-butyl-4-(2'-thenoyl)phenol [INN: PRIFELONE], alpha-cyano-1-methyl-beta-oxopyrrole-2-propionanilide [INN: PRINOMIDE], 3-[4-(2-hydroxyethyl)-1-piperazinyl]-propyl-D,L-4-benzamido-N,N-dipropylglutaramat 1-(p-chlorobenzoyl)-5-methoxy-2-methylindole-3-acetate (ester) [INN: PROGLUMETACIN], 7-methyl-1-(1-methylethyl)-4-phenyl-2(1H)quinazolinone [INN: PROQUAZONE], 7-methoxy-alpha,10-dimethylphenothiazine-2-acetic acid

[INN: PROTIZINIC] ACID], 2-[[2-(p-chlorophenyl)-4-methyl-5-oxazolyl]methoxy]-2-methylpropionic acid [INN: ROMAZARIT], o-hydroxybenzamide [SALICYLAMIDE], 2-hydroxybenzoic acid [SALICYLIC ACID], N-acetyl-L-cysteine salicylate (ester); acetate (ester) [INN: SALMISTEINE], N-acetyl-L-cysteine salicylate (ester) [INN: SALNACEDIN], 2-hydroxybenzoic acid 2-carboxyphenyl ester [INN: SALSALATE], 4-[1-(2-fluorobiphenyl-4-yl)ethyl]-N-methylthiazole-2-amine [Research Code: SM-8849], (Z)-5-fluoro-2-methyl-1-[p-(methylsulfinyl)benzylidene]indene-3-acetic acid [INN: SULINDAC], p-2-thenoylhydratropic acid [INN: SUPROFEN] 2-(4-(3-methyl-2-butenyl)phenyl)propionic acid [Research Code: TA-60], phthalidyl 2-(alpha,alpha,alpha-trifluoro-m-toluidino)nicotinate [INN: TALNIFLUMATE], (Z)-5-chloro-3-(2-thenoyl)-2-oxoinidole-1-carboxamide [INN: TENIDAP], 2-thiophenecarboxylic acid, ester with salicylic acid [INN: TENOSAL], 4-hydroxy-2-methyl-N-2-pyridyl-2H-thieno[2,3-e]-1,2-thiazine-3-carboxamide [INN: TENOXICAM], 5-(4-chlorophenyl)-N-hydroxy-1-(4-methoxyphenyl)-N-methyl-1H-pyrazole-3-propionamide [INN: TEPOXALIN], alpha-(5-benzoyl-2-thienyl)propionic acid [INN: TIAPROFENIC ACID], 5-chloro-3-[4-(2-hydroxyethyl)-1-piperazinyl]carbonylmethyl-2-benzo-thiazolin one [INN: TIARAMIDE], 2-(2-methyl-5H-[1]benzopyrano[2,3-b]pyridin-7-yl)-propionic acid N,N-dimethylcarbamoylmethyl ester [INN: TILNOPROFEN ARBAMEL], 1-Cyclohexyl-2-(2-methyl-4-quinolyl)-3-(2-thiazolyl)guanidine [INN: TIMEGADINE], 2-amino-6-benzyl-4,5,6,7-tetrahydrothieno[2,3-c]pyridine [INN: TINORIDINE], N-(3-chloro-o-tolyl)anthranilic acid [INN: TOLFENAMIC ACID], 1-methyl-5-(4-methylbenzoyl)-1H-pyrrole-2-acetic acid [INN: TOLMETIN], hydroxybis[alpha-methyl-4-(2-methylpropyl)benzene acetato-O]-aluminium [Research Code: U-18573-G], N-(3-trifluoromethylphenyl)-anthranilic acid n-butyl ester [INN: UFENAMATE], 2-[4-[3-(hydroxyimino)cyclohexyl]phenyl]propionic acid [INN: XIMOPROFEN], 2-(10,11-dihydro-10-oxo-dibenz[b,f]thiepin-2-yl-propionic acid [INN: ZALTOPROFEN], 2-[4-(2-thiazolyloxy)phenyl]-propionic acid [INN: ZOLIPROFEN] and their pharmaceutically acceptable derivatives, for simultaneous, sequential or separate use in therapy.

In a fifth aspect—which is an embodiment of the forth aspect—the invention provides a pharmaceutical product comprising, in combination, a preparation of a first active ingredient which is a PDE4-inhibitor selected from cis-[4-Cyano-4-(3-cyclopentyloxy-4-methoxyphenyl)cyclohexane-1-carboxylic acid [INN: CILOMILAST], 3-Cyclopropylmethoxy-4-difluoromethoxy-N-(3,5-dichloropyrid-4-yl)-benzamide [INN: ROFLUMILAST] and their pharmaceutically acceptable derivatives, and a preparation of a second active ingredient which is a conventional NSAID selected from 2-(acetyloxy)benzoic acid [ACETYLSALICYLIC ACID], 2-[(2,6-dichlorophenyl)amino]benzeneacetic acid [INN: DICLOFENAC], alpha-p-isobutylphenylpropionic acid [INN: IBUPROFEN],], 1-(4-chlorobenzoyl)-5-methoxy-2-methyl-1H-indole-3-acetic acid [INN: INDOMETACIN], (plus)-6-methoxy-alpha-methyl-2-naphthalineacetic acid [INN: NAPROXEN], 4-hydroxy-2-methyl-N-2-pyridyl-2H-1,2-benzothiadiazin-3-carboxamide 1,1-dioxide [INN: PIROXICAM] and their pharmaceutically acceptable derivatives, for simultaneous, sequential or separate use in therapy.

In a sixth aspect—which is another embodiment of the forth aspect—the invention provides a pharmaceutical product comprising, in combination, a preparation of a first active ingredient which is selected from 3-Cyclopropylmethoxy-4-difluoromethoxy-N-(3,5-dichloropyrid-4-yl)-benzamide [INN: ROFLUMILAST] and its pharmaceutically acceptable derivatives, and a preparation of a second active ingredient which is selected from 2-[(2,6-dichlorophenyl)amino]benzeneacetic acid [INN: DICLOFENAC] and its pharmaceutically acceptable derivatives, for simultaneous, sequential or separate use in therapy.

In a seventh aspect, the invention provides a kit comprising a preparation of a first active ingredient which is a PDE4-inhibitor selected from CDC-998, SH-636, D-4396, IC-485, CC-1088 and 3,5-dichloro-4-[8-methoxy-2-(trifluoromethyl)quinoline-5-ylcarboxamidolpyridine-1-oxide [Research Code: SCH351591], 3-[3-(cyclopentyloxy)-4-methoxybenzyl]-6-(ethylamino)-8-isopropyl-3H-purine [Research-Code: V-11294A], N-[9-methyl-4-oxo-1-phenyl-3,4,6,7-tetrahydropyrrolo[3,2,1-jk][1,4]benzodiazepin-3(R)-yl]pyridine-4-carboxamide [Research-Code: CI-1018, N-(3,5-dichloro-4-pyridinyl)-2-[1-(4-fluorobenzyl)-5-hydroxy-1H-indol-3-yl]-2-oxoacetamide [Research-Code: AWD-12-281], N-(3,5-di-chloropyridin-4-yl)-2-[5-fluoro-1-(4-fluorobenzyl)-1H-indol-3-yl]-2-oxoacetamide [Research-Code: AWD-12-343], 8-Amino-1,3-bis(cyclopropylmethyl)xanthine [INN: CIPAMFYLLINE], Tetrahydro-5-[4-methoxy-3-[(1S,2S,4R)-2-norbornyloxy]phenyl]-2(1H)-pyrimidone [INN: ATIZORAM], β-[3-(Cyclopentyloxy)-4-methoxyphenyl]-1,3-dihydro-1,3-dioxo-2H-isoindole-2-propanamide [Research-Code: CDC-801], Methanesulfonic acid 2-(2,4-dichlorophenylcarbonyl)-3-ureidobenzo-furan-6-yl ester [INN: LIRIMILAST], N-(3,5-dichloropyrid-4-yl)-3-cyclopentyloxy-4-methoxybenzamide [INN: PICLAMILAST], cis-[4-Cyano-4-(3-cyclopentyloxy-4-methoxyphenyl)cyclohexane-1-carboxylic acid [INN: CILOMILAST], 3-Cyclopropyl]ethoxy-4-difluoromethoxy-N-(3,5-dichloropyrid-4-yl)-benzamide [INN: ROFLUMILAST] and their pharmaceutically acceptable derivatives, a preparation of a second active ingredient which is a conventional NSAID selected from glycolic acid [o-(2,6-dichloroanilino)phenyl]acetate(ester) [INN: ACECLOFENAC]; 1-(4-chlorobenzoyl)-5-methoxy-2-methyl-1H-indole-3-acetic acid carboxymethyl ester [INN: ACEMETACIN]; 2-(acetyloxy)benzoic acid [ACETYLSALICYLIC ACID], 2-methoxyphenyl-alpha-methyl-4-(isobutyl)phenylacetate [Research Code: AF-2259], (4-allyloxy-3-chlorophenyl)acetic acid [INN: ALCLOFENAC], p-[(2-methylallyl)amino]hydratropic acid [INN: ALMINOPROFEN], 2-amino-3-benzoylphenylacetic acid [INN: AMFENAC], (plus/minus)-4-(1-hydroxyethoxy)-2-methyl-N-2-pyridyl-2H-1,2-benzothiazine-3-carboxamide ethylcarbonate (ester), 1,1-dioxide [INN: AMPIROXICAM], 2-methoxyphenyl-1-methyl-5-(p-methylbenzoyl)pyrrol-2-acetamido-acetate [INN: AMTOLMETINGUACIL], (plus/minus)-2,3-dihydro-5-(4-methoxybenzoyl)-1H pyrrolizine-1-carboxylic acid [INN: ANIROLAC], 2-[4-(alpha,alpha,alpha-trifluoro-m-tolyl)-1-piperazinyl]ethyl-N-(7-trifluoromethyl-4-quinolyl)anthranilate [INN: ANTRAFENINE], 5-(dimethylamino)-9-methyl-2-propyl-1H-pyrazolo[1,2-a][1,2,4]benzo-triazine-1,3(2H)-dione [INN: AZAPROPAZONE], 4-acetamidophenyl salicylate acetate [INN: BENORILATE], 2-(8-methyl-10,11-dihydro-11-oxodibenz[b,f]oxepin-2-yl)propionic acid [INN: BERMOPROFEN], 2-[(1-benzyl-1H-indazol-3-yl)methoxy]-2-methylpropionic acid [INN: BINDARIT], [2-amino-3-(p-bromobenzoyl)phenyl]acetic acid [INN: BROMFENAC], 3-(3-chloro-4-cyclohexylbenzoyl)propionic acid [INN: BUCLOXIC ACID], 5-butyl-1-cyclohexylbarbituric acid [INN: BUCOLOM], 4-butoxy-N-hydroxybenzeneacetamide [INN: BUFEXAMAC]; butylmalonic acid mono(1,2-diphenylhydrazide) [INN:

BUMADIZONE], alpha-ethyl-4-(2-methylpropyl)benzeneacetic acid [INN: BUTIBUFEN], 2-(4-biphenylyl)butyric acid, trans-4-phenylcyclohexylamine salt (1:1) [INN: BUTIXIRATE], 2-(acetyloxy)-benzoic acid, calcium salt, compound with urea (1:1) [INN: CARBASALATE CALCIUM], (plus/minus)-6-chloro-alpha-methylcarbazole-2-acetic acid [INN: CARPROFEN], 1-cinnamoyl-5-methoxy-2-methylindole-3-acetic acid [INN: CINMETACIN], N-(2-pyridyl)-2-methyl-4-cinnamoyloxy-2H-1,2-benzothiazine-3-carboxamide-1,1-dioxide [INN: CINNOXICAM], 6-chloro-5-cyclohexyl-1-indancarboxylic acid [INN: CLIDANAC], 2-[4-(p-chlorophenyl)benzyloxy]-2-methylpropionic acid [INN: CLOBUZARIT], 5-methoxy-2-methyl-3-indolylacetohydroxamic acid [INN: DEBOXAMET], (S)-(+)-p-iso-butylhydratropic acid [INN: DEXIBUPROFEN], (+)-(S)-m-benzoylhydratropic acid [INN: DEXKETOPROFEN], 2-[(2,6-dichlorophenyl)amino]benzeneacetic acid [INN: DICLOFENAC], 2',4'-Difluoro-4-hydroxy-3-biphenylcarboxylic acid [INN: DIFLUNISAL], 4-(2,6-dichloroanilino)-3-thiopheneacetic acid [INN: ELTENAC], N-beta-phenethyl-anthranilic acid [INN: ENFENAMIC ACID] salicylic acid acetate, ester with beta-hydroxy p-acetophenetidide [INN: ETERSALATE], 1,8-diethyl-1,3,4,9-tetrahydropyrano[3,4-b]indole-1-acetic acid [INN: ETODOLAC], 2-[[3-(trifluoromethyl)phenyl]amino]benzoic acid 2-(2-hydroxyethoxy)-ethyl ester [INN: ETOFENAMATE], p-chlorobenzoic acid, ester with 4-butyl-4-(hydroxymethyl)-1,2-diphenyl-3,5-pyrazolidinedione [INN: FECLOBUZONE], 4-biphenylacetic acid [INN: FELBINAC], 3-(4-biphenylylcarbonyl)propionic acid [INN: FENBUFEN], [o-(2,4-dichlorophenoxy)phenyl]acetic acid [INN: FENCLOFENAC], (plus/minus)-m-phenoxyhydratropic acid [INN: FENOPROFEN], 4-(p-chlorophenyl)-2-phenyl-5-thiazoleacetic acid [INN: FENTIAZAC], (plus/minus)-alpha-[[(2-hydroxy-1,1-dimethylethyl)amino]methyl]-benzyl alcohol [INN: FEPRADINOL], 4-(2',4'-difluorobiphenylyl)-4-oxo-2-methylbutanoic acid [INN: FLOBUFEN], N-(alpha,alpha,alpha-trifluoro-m-tolyl)anthranilic acid [INN: FLUFENAMIC ACID], (plus)-2-(p-fluorophenyl)-alpha-methyl-5-benzoxazoleacetic acid [INN: FLUNOXAPROFEN], 2-fluoro-alpha-methyl-4-biphenylacetic acid [INN: FLURBIPROFEN], (plus/minus)-2-(2-fluoro-4-biphenylyl)propionic acid 1 (acetoxy)ethyl ester [INN: FLURBIPROFEN AXETIL], 2-ethyl-2,3-dihydro-5-benzofuranacetic acid [INN: FUROFENAC], 2-[4-(2'-furoyl)phenyl]propionic acid [INN: FURPROFEN], 2-[2-[1-(p-chlorobenzyl)-5-methoxy-2-methylindol-3-yl]acetamido]-2-deoxy-D-glucose [INN: GLUCAMETACIN], 2-(2-fluorobiphenyl-4-yl)propionic acid 4-nitrooxybutylester [Research Code: HCT-1026], (p-isobutylphenyl)acetic acid [INN: IBUFENAC], alpha-p-isobutylphenylpropionic acid [INN: IBUPROFEN], methyl 4-(3-thienyl)phenyl-alpha-methylacetate [Research Code: IDPH-8261], (plus/minus)-2-[p-(1-oxo-2-isoindolinyl)phenyl]butyric acid [INN: INDOBUFEN], 1-(4-chlorobenzoyl)-5-methoxy-2-methyl-1H-indole-3-acetic acid [INN: INDOMETACIN], 1-(4-chlorobenzoyl)-5-methoxy-2-methyl-1H-indole-3-acetic acid, 3,7,11-trimethyl-2,6,10-dodecatrienyl ester [INN: INDOMETACIN FARNESIL], p-(1-oxo-2-isoindolinyl)hydratropic acid [INN: INDOPROFEN], 2-(10-methoxy-4H-benzo[4,5]cyclohepta[1,2-b]thiophen-4-ylidene)-acetic acid [Research Code: IX-207-887], m-benzoylhydratropic acid [INN: KETOPROFEN], (DL)-5-benzoyl-3H-1,2-dihydropyrrolo[1,2-a]pyrrole-1-carboxylic acid [INN: KETOROLAC], 2,3-dihydro-5-hydroxy-6-[2-(hydroxymethyl)cinnamyl]benzofuran [Research Code: L-651896], N-(2-carboxyphenyl)-4-chloroanthranilic acid [INN: LOBENZARIT], 3-(p-chlorophenyl)-1-phenylpyrazole-4-acetic acid [INN: LONAZOLAC], 6-chloro-4-hydroxy-2-methyl-N-2-pyridyl-2H-thieno[2,3-e]-1,2-thiazine-3-carboxamide 1,1-dioxide [INN: LORNOXICAM], 2-[4-(2-oxocyclopentan-1-ylmethyl)phenyl]-propionate [INN: LOXOPROFEN], 2(R)-[4-(3-methyl-2-thienyl)phenyl]propionic acid [Research Code: M-5010], N-(2,3-xylyl)anthranilic acid [INN: MEFENAMIC ACID], 4-hydroxy-2-methyl-N-(5-methyl-2-thiazolyl)-2H-1,2-benzothiazine-3-carboxamide 1,1-dioxide [INN: MELOXICAM], 5-aminosalicylic acid [INN: MESALAZINE], (2,2-dimethyl-6-(4-chlorophenyl)-7-phenyl-2,3-dihydro-1H-pyrrolizin-5-yl)-acetic acid [Research Code: ML-3000], 3,4-bis(4-methoxyphenyl)-5-isoxazoleacetic acid [INN: MOFEZOLAC], 4-(6-methoxy-2-naphthyl)-2-butanone [INN: NABUMETONE], (plus)-6-methoxy-alpha-methyl-2-naphthalineacetic acid [INN: NAPROXEN], 2-[3-(trifluoromethyl)anilino]nicotinic acid [INN: NIFLUMIC ACID], 5,5'-azodisalicylic acid [INN: OLSALAZINE], alpha-methyl-4-[(2-oxocyclohexylidene)methyl]benzene acetic acid [INN: PELUBIPROFEN], 2-(p-isobutylphenyl)propionic acid 2-pyridyl-methyl ester [INN: PIMEPROFEN], 4-(p-chlorophenyl)-1-(p-fluorophenyl)pyrazole-3-acetic acid [INN: PIRAZOLAC], 4-hydroxy-2-methyl-N-2-pyridyl-2H-1,2-benzothiadiazin-3-carboxamide 1,1-dioxide [INN: PIROXICAM], 3-chloro-4-(3-pyrrolin-1-yl)hydratropic acid [INN: PIRPROFEN], 2-[5H-(1)benzopyrano]2,3-b]pyridin-7-yl]propionic acid [INN: PRANOPROFEN], 2,6-di-tert-butyl-4-(2'-thenoyl)phenol [INN: PRIFELONE], alpha-cyanomethyl-beta-oxopyrrole-2-propionanilide [INN: PRINOMIDE], 3-[4-(2-hydroxyethyl)-1-piperazinyl]-propyl-D,L-4-benzamido-N,N-dipropylglutaramat 1-(p-chlorobenzoyl)-5-methoxy-2-methylindole-3-acetate (ester) [INN: PROGLUMETACIN], 7-methyl-1-(1-methylethyl)-4-phenyl-2(1H)quinazolinone [INN: PROQUAZONE], 7-methoxy-alpha,10-dimethylphenothiazine-2-acetic acid [INN: PROTIZINIC] ACID], 2-[[2-(p-chlorophenyl)-4-methyl-5-oxazolyl]methoxy]-2-methylpropionic acid [INN: ROMAZARIT], o-hydroxybenzamide [SALICYLAMIDE], 2-hydroxy-benzoic acid [SALICYLIC ACID], N-acetyl-L-cysteine salicylate (ester), acetate (ester) [INN: SALMISTEINE], N-acetyl-L-cysteine salicylate (ester) [INN: SALNACEDIN], 2-hydroxybenzoic acid 2-carboxyphenyl ester [INN: SALSALATE], 4-[1-(2-fluorobiphenyl-4-yl)ethyl]-N-methylthiazole-2-amine [Research Code: SM-8849], (Z)-5-fluoro-2-methyl-1-[p-(methylsulfinyl)benzylidene]indene-3-acetic acid [INN: SULINDAC], p-2-thenoylhydratropic acid [INN: SUPROFEN] 2-(4-(3-methyl-2-butenyl)phenyl)-propionic acid [Research Code: TA-60], phthalidyl 2-(alpha,alpha,alpha-trifluoro-m-toluidino)nicotinate [INN: TALNIFLUMATE], (Z)-5-chloro-3-(2-thenoyl)-2-oxoindole-1-carboxamide [INN: TENIDAP], 2-thiophenecarboxylic acid, ester with salicylic acid [INN: TENOSAL], 4-hydroxy-2-methyl-N-2-pyridyl-2H-thieno[2,3-e]-1,2-thiazine-3-carboxamide [INN: TENOXICAM], 5-(4-chlorophenyl)-N-hydroxy-1-(4-methoxyphenyl)-N-methyl-1H-pyrazole-3-propionamide [INN: TEPOXALIN], alpha-(5-benzoyl-2-thienyl)propionic acid [INN: TIAPROFENIC ACID], 5-chloro-3-[4-(2-hydroxyethyl)-1-piperazinyl]carbonylmethyl-2-benzo-thiazolin one [INN: TIARAMIDE], 2-(2-methyl-5H-[1]benzopyrano[2,3-b]pyridin-7-yl)-propionic acid N,N-dimethylcarbamoylmethyl ester [INN: TILNOPROFEN ARBAMEL], 1-Cyclohexyl-2-(2-methyl-4-quinolyl)-3-(2-thiazolyl)guanidine [INN: TIMEGADINE], 2-amino-6-benzyl-4,5,6,7-tetrahydrothieno[2,3-c]pyridine [INN: TINORIDINE], N-(3-chloro-o-tolyl)anthranilic acid [INN: TOLFENAMIC ACID], 1-methyl-5-(4-methylbenzoyl)-1H-pyrrole-2-acetic acid [INN:

TOLMETIN], hydroxybis[alpha-methyl-4-(2-methylpropyl) benzene acetato-O]-aluminium [Research Code: U-18573-G], N-(3-trifluoromethylphenyl)-anthranilic acid n-butyl ester [INN: UFENAMATE], 2-[4-[3-(hydroxyimino)cyclohexyl]-phenyl]propionic acid [INN: XIMOPROFEN], 2-(10, 11-dihydro-10-oxo-dibenz[b,f]thiopin-2-yl-propionic acid [INN: ZALTOPROFEN], 2-[4-(2-thiazolyloxy)phenyl]-propionic acid [INN: ZOLIPROFEN] and their pharmaceutically acceptable derivatives, and instructions for the simultaneous, sequential or separate administration of the preparations to a patient in need thereof.

In a eighth aspect—which is an embodiment of the seventh aspect—the invention provides a kit comprising a preparation of a first active ingredient which is a PDE4-inhibitor selected from cis-[4-Cyano-4-(3-cyclopentyloxy-4-methoxyphenyl) cyclohexane-1-carboxylic acid [INN: CILOMILAST], 3-Cyclopropylmethoxy-4-difluoromethoxy-N-(3,5-dichloropyrid-4-yl)-benzamide [INN: ROFLUMILAST] and their pharmaceutically acceptable derivatives, a preparation of a second active ingredient which is conventional NSAID selected from 2-(acetyloxy)benzoic acid [ACETYLSALICYLIC ACID], 2-[(2,6-dichlorophenyl)amino]benzeneacetic acid [INN: DICLOFENAC], alpha-p-isobutylphenylpropionic acid [INN: IBUPROFEN],], 1-(4-chlorobenzoyl)-5-methoxy-2-methyl-1H-indole-3-acetic acid [INN: INDOMETACIN], (plus)-6-methoxy-alpha-methyl-2-naphthalineacetic acid [INN: NAPROXEN], 4-hydroxy-2-methyl-N-2-pyridyl-2H-1,2-benzothiadiazin-3-carboxamide 1,1-dioxide [INN: PIROXICAM] and their pharmaceutically acceptable derivatives, and instructions for the simultaneous, sequential or separate administration of the preparations to a patient in need thereof.

In a ninth aspect—which is another embodiment of the seventh aspect—the invention provides a kit comprising a preparation of a first active ingredient which is selected from 3-Cyclopropylmethoxy-4-difluoromethoxy-N-(3,5-dichloropyrid-4-yl)-benzamide [INN: ROFLUMILAST] and its pharmaceutically acceptable derivatives, a preparation of a second active ingredient which is selected from 2-[(2,6-dichlorophenyl)amino]benzeneacetic acid [INN: DICLOFENAC] and its pharmaceutically acceptable derivatives, and instructions for the simultaneous, sequential or separate administration of the preparations to a patient in need thereof.

It has been found that the choice of active ingredients according to the invention is advantageous because it results in a beneficial antiinflammatory effect while simultaneously minimizing gastrointestinal side effects which are inevitably associated with the use of the conventional NSAIDs.

The pharmaceutical composition of the present invention may be prepared by mixing the first active ingredient with the second active ingredient.

In the above-mentioned mixing process the first active ingredient and the second active ingredient can
a) in a first step be mixed as such, afterwards be processed with pharmaceutically acceptable auxiliaries and/or excipients and finally pressed to tablets or caplets or
b) in a first step separately be processed with pharmaceutically acceptable auxiliaries and/or excipients to give granules or pellets containing each only one of the two active ingredients; the pellets or granules for their part then can be mixed in an appropriate ratio and either be pressed—optionally with further pharmaceutically acceptable auxiliaries and/or excipients—to give for example, tablets or caplets, or can be filled in more or less loose form in capsules.

Therefore, in a tenth aspect of the present invention, there is provided a process for the preparation of a pharmaceutical composition which comprises mixing a first active ingredient which is a PDE4-inhibitor selected from CDC-998, SH-636, D-4396, IC-485, CC-1088 and 3,5-dichloro-4-[8-methoxy-2-(trifluoromethyl)quinoline-5-ylcarboxamido]pyridine-1-oxide [Research Code: SCH351591], 3-[3-(cyclopentyloxy)-4-methoxybenzyl]-6-(ethylamino)-8-isopropyl-3H-purine [Research-Code: V-11294A], N-[9-methyl-4-oxo-1-phenyl-3,4,6,7-tetrahydropyrrolo[3,2,1-jk][1,4]benzo-diazepin-3 (R)-yl]pyridine-4-carboxamide [Research-Code: CI-1018, N-(3,5-dichloro-4-pyridinyl)-2-[1-(4-fluorobenzyl)-5-hydroxy-1H-indol-3-yl]-2-oxoacetamide [Research-Code: AWD-12-281], N-(3,5-dichloropyridin-4-yl)-2-[5-fluoro-1-(4-fluorobenzyl)-1H-indol-3-yl]-2-oxoacetamide [Research-Code: AWD-12-343], 8-Amino-1,3-bis(cyclopropylmethyl) xanthine [INN: CIPAMFYLLINE], Tetrahydro-5-[4-methoxy-3-[(1S,2S,4R)-2-norbornyloxy]phenyl]-2(1H)-pyrimidone [INN: ATIZORAM], β-[3-(Cyclopentyloxy)-4-methoxyphenyl]-1,3-dihydro-1,3-dioxo-2H-isoindole-2-propanamide [Research-Code: CDC-801], Methanesulfonic acid 2-(2,4-dichlorophenylcarbonyl)-3-ureidobenzo-furan-6-yl ester [INN: LIRIMILAST], N-(3,5-dichloropyrid-4-yl)-3-cyclopentyloxy-4-methoxybenzamide [INN: PICLAMILAST], cis-[4-Cyano-4-(3-cyclopentyloxy-4-methoxyphenyl)cyclohexane-1-carboxylic acid [INN: CILOMILAST], 3-Cyclopropylmethoxy-4-difluoromethoxy-N-(3,5-dichloropyrid-4-yl)-benzamide [INN: ROFLUMILAST] and their pharmaceutically acceptable derivatives, with a second active ingredient which is a conventional NSAID selected from glycolic acid [o-(2,6-dichloroanilino)phenyl]acetate (ester) [INN: ACECLOFENAC]; 1-(4-chlorobenzoyl)-5-methoxy-2-methyl-1H-indole-3-acetic acid carboxymethyl ester [INN: ACEMETACIN]; 2-(acetyloxy)benzoic acid [ACETYLSALICYLIC ACID], 2-methoxyphenyl-alpha-methyl-4-(isobutyl)phenylacetate [Research Code: AF-2259], (4-allyloxy-3-chlorophenyl)acetic acid [INN: ALCLOFENAC], p-[(2-methylallyl)amino]-hydratropic acid [INN: ALMINOPROFEN], 2-amino-3-benzoylphenylacetic acid [INN: AMFENAC], (plus/minus)-4-(1-hydroxyethoxy)-2-methyl-N-2-pyridyl-2H-1,2-benzothiazine-3-carboxamide ethylcarbonate (ester), 1,1-dioxide [INN: AMPIROXICAM], 2-methoxyphenyl-1-methyl-5-(p-methylbenzoyl)pyrrol-2-acetamido-acetate [INN: AMTOLMETINGUACIL]; (plus/minus)-2,3-dihydro-5-(4-methoxybenzoyl)-1H pyrrolizine-1-carboxylic acid [INN: ANIROLAC], 2-[4-(alpha,alpha,alpha-trifluoro-m-tolyl)-1-piperazinyl]ethyl-N-(7-trifluoromethyl-4-quinolyl)anthranilate [INN: ANTRAFENINE], 5-(dimethylamino)-9-methyl-2-propyl-1H-pyrazolo[1,2-a][1,2,4]benzo-triazine-1,3 (2H)-dione [INN: AZAPROPAZONE], 4-acetamidophenyl salicylate acetate [INN: BENORILATE], 2-(8-methyl-10,11-dihydro-11-oxodibenz[b,f]oxepin-2-yl)propionic acid [INN: BERMOPROFEN], 2-[(1-benzyl-1H-indazol-3-yl)methoxy]-2-methylpropionic acid [INN: BINDARIT], [2-amino-3-(p-bromobenzoyl)phenyl]acetic acid [INN: BROMFENAC], 3-(3-chloro-4-cyclohexylbenzoyl)propionic acid [INN: BUCLOXIC ACID], 5-butyl-1-cyclohexylbarbituric acid [INN: BUCOLOM], 4-butoxy-N-hydroxybenzeneacetamide [INN: BUFEXAMAC], butylmalonic acid mono (1,2-diphenylhydrazide) [INN: BUMADIZONE], alpha-ethyl-4-(2-methylpropyl)benzeneacetic acid [INN: BUTIBUFEN], 2-(4-biphenylyl)butyric acid, trans-4-phenylcyclohexylamine salt (1:1) [INN: BUTIXIRATE], 2-(acetyloxy)-benzoic acid, calcium salt, compound with urea (1:1) [INN: CARBASALATE CALCIUM], (plus/minus)-6-chloro-alpha-methylcarbazole-2-acetic acid [INN:

CARPROFEN], 1-cinnamoyl-5-methoxy-2-methylindole-3-acetic acid [INN: CINMETACIN], N-(2-pyridyl)-2-methyl-4-cinnamoyloxy-2H-1,2-benzothiazine-3-carboxamide-1,1-dioxide [INN: CINNOXICAM], 6-chloro-5-cyclohexyl-1-indancarboxylic acid [INN: CLIDANAC], 2-[4-(p-chlorophenyl)benzyloxy]-2-methylpropionic acid [INN: CLOBUZARIT], 5-methoxy-2-methyl-3-indolylacetohydroxamic acid [INN: DEBOXAMET], (S)-(+)-p-isobutylhydratropic acid [INN: DEXIBUPROFEN], (+)-(S)-m-benzoylhydratropic acid [INN: DEXKETOPROFEN], 2-[(2,6-dichlorophenyl)amino]benzeneacetic acid [INN: DICLOFENAC], 2',4'-Difluoro-4-hydroxy-3-biphenylcarboxylic acid [INN: DIFLUNISAL], 4-(2,6-dichloroanilino)-3-thiopheneacetic acid [INN: ELTENAC], N-beta-phenethyl-anthranilic acid [INN: ENFENAMIC ACID] salicylic acid acetate, ester with beta-hydroxy p-acetophenetidide [INN: ETERSALATE], 1,8-diethyl-1,3,4,9-tetrahydropyrano[3,4-b]indole-1-acetic acid [INN: ETODOLAC], 2-[[3-(trifluoromethyl)phenyl]-amino]benzoic acid 2-(2-hydroxyethoxy)-ethyl ester [INN: ETOFENAMATE], p-chlorobenzoic acid, ester with 4-butyl-4-(hydroxymethyl)-1,2-diphenyl-3,5-pyrazolidinedione [INN: FECLOBUZONE], 4-biphenylacetic acid [INN: FELBINAC], 3-(4-biphenylylcarbonyl)propionic acid [INN: FENBUFEN], [o-(2,4-dichlorophenoxy)phenyl]acetic acid [INN: FENCLOFENAC], (plus/minus)-m-phenoxyhydratropic acid [INN: FENOPROFEN], 4-(p-chlorophenyl)-2-phenyl-5-thiazoleacetic acid [INN: FENTIAZAC], (plus/minus)-alpha-[[(2-hydroxy-1,1-dimethylethyl)amino]methyl]-benzyl alcohol [INN: FEPRADINOL], 4-(2',4'-difluorobiphenylyl)-4-oxo-2-methylbutanoic acid [INN: FLOBUFEN], N-(alpha,alpha,alpha-trifluoro-m-tolyl)anthranilic acid [INN: FLUFENAMIC ACID], (plus)-2-(p-fluorophenyl)-alpha-methyl-5-benzoxazoleacetic acid [INN: FLUNOXAPROFEN], 2-fluoro-alpha-methyl-4-biphenylacetic acid [INN: FLURBIPROFEN], (plus/minus)-2-(2-fluoro-4-biphenylyl)propionic acid 1 (acetoxy)ethyl ester [INN: FLURBIPROFEN AXETIL], 2-ethyl-2,3-dihydro-5-benzofuranacetic acid [INN: FUROFENAC], 2-[4-(2'-furoyl)phenyl]propionic acid [INN: FURPROFEN], 2-[2-[1-(p-chlorobenzoyl)-5-methoxy-2-methylindol-3-yl]acetamido]-2-deoxy-D-glucose [INN: GLUCAMETACIN], 2-(2-fluorobiphenyl-4-yl)propionic acid 4-nitrooxybutylester [Research Code: HCT-1026], (p-isobutylphenyl)acetic acid [INN: IBUFENAC], alpha-p-isobutylphenylpropionic acid [INN: IBUPROFEN], methyl 4-(3-thienyl)phenyl-alpha-methyl-acetate [Research Code: IDPH-8261], (plus/minus)-2-[p-(1-oxo-2-isoindolinyl)phenyl]butyric acid [INN: INDOBUFEN], 1-(4-chlorobenzoyl)-5-methoxy-2-methyl-1H-indole-3-acetic acid [INN: INDOMETACIN], 1-(4-chlorobenzoyl)-5-methoxy-2-methyl-1H-indole-3-acetic acid, 3,7,11-trimethyl-2,6,10-dodecatrienyl ester [INN: INDOMETACIN FARNESIL], p-(1-oxo-2-isoindolinyl)hydratropic acid [INN: INDOPROFEN], 2'-(10-methoxy-4H-benzo[4,5]cyclohepta[1,2-b]thiophen-4-ylidene)-acetic acid [Research Code: IX-207-887], m-benzoylhydratropic acid [INN: KETOPROFEN], (DL)-5-benzoyl-3H-1,2-dihydropyrrolo[1,2-a]pyrrole-1-carboxylic acid [INN: KETOROLAC], 2,3-dihydro-5-hydroxy-6-[2-(hydroxymethyl)cinnamyl]benzofuran [Research Code: L-651896], N-(2-carboxyphenyl)-4-chloroanthranilic acid [INN: LOBENZARIT], 3-(p-chlorophenyl)-1-phenylpyrazole-4-acetic acid [INN: LONAZOLAC], 6-chloro-4-hydroxy-2-methyl-N-2-pyridyl-2H-thieno[2,3-e]-1,2-thiazine-3-carboxamide 1,1-dioxide [INN: LORNOXICAM], 2-[4-(2-oxocyclopentan-1-ylmethyl)phenyl]-propionate [INN: LOXOPROFEN], 9(R)-[4-(3-methyl-2-thienyl)phenyl]propionic acid [Research Code: M-5010], N-(2,3-xylyl)anthranilic acid [INN: MEFENAMIC ACID], 4-hydroxy-2-methyl-N-(5-methyl-2-thiazolyl)-2H-1,2-benzothiazine-3-carboxamide 1,1-dioxide [INN: MELOXICAM], 5-aminosalicylic acid [INN: MESALAZINE], (2,2-dimethyl-6-(4-chlorophenyl)-7-phenyl-2,3-dihydro-1H-pyrrolizin-5-yl)-acetic acid [Research Code: ML-3000], 3,4-bis-(4-methoxyphenyl)-5-isoxazoleacetic acid [INN: MOFEZOLAC], 4-(6-methoxy-2-naphthyl)-2-butanone [INN: NABUMETONE], (plus)-6-methoxy-alpha-methyl-2-naphthalineacetic acid [INN: NAPROXEN], 2-[3-(trifluoromethyl)anilino]nicotinic acid [INN: NIFLUMIC ACID], 5,5'-azodisalicylic acid [INN: OLSALAZINE], alpha-methyl-4-[(2-oxocyclohexylidene)methyl]benzene acetic acid [INN: PELUBIPROFEN], 2-(p-isobutylphenyl)propionic acid 2-pyridyl-methyl ester [INN: PIMEPROFEN], 4-(p-chlorophenyl)-1-(p-fluorophenyl)pyrazole-3-acetic acid [INN: PIRAZOLAC], 4-hydroxy-2-methyl-N-2-pyridyl-2H-1,2-benzothiadiazin-3-carboxamide 1,1-dioxide [INN: PIROXICAM], 3-chloro-4-(3-pyrrolin-1-yl)hydratropic acid [INN: PIRPROFEN], 2-[5H-(1)benzopyrano]2,3-b]pyridin-7-yl]propionic acid [INN: PRANOPROFEN], 2,6-di-tert-butyl-4-(2'-thenoyl)phenol [INN: PRIFELONE], alpha-cyano-1-methyl-beta-oxopyrrole-2-propionanilide [INN: PRINOMIDE], 3-[4-(2-hydroxyethyl)-1-piperazinyl]-propyl-D,L-4-benzamidor-N,N-dipropylglutaramat 1-(p-chlorobenzoyl)-5-methoxy-2-methylindole-3-acetate (ester) [INN: PROGLUMETACIN], 7-methyl-1-(1-methylethyl)-4-phenyl-2(1H)quinazolinone [INN: PROQUAZONE], 7-methoxy-alpha,10-dimethylphenothiazine-2-acetic acid [INN: PROTIZINIC] ACID], 2-[[2-(p-chlorophenyl)-4-methyl-5-oxazolyl]methoxy]-2-methylpropionic acid [INN: ROMAZARIT], o-hydroxybenzamide [SALICYLAMIDE], 2-hydroxybenzoic acid [SALICYLIC ACID], N-acetyl-L-cysteine salicylate (ester), acetate (ester) [INN: SALMISTEINE], N-acetyl-L-cysteine salicylate (ester) [INN: SALNACEDIN], 2-hydroxybenzoic acid 2-carboxyphenyl ester [INN: SALSALATE], 4-[1-(2-fluorobiphenyl-4-yl)ethyl]-N-methylthiazole-2-amine [Research Code: SM-8849], (Z)-5-fluoro-2-methyl-1-[p-(methylsulfinyl)benzylidene]indene-3-acetic acid [INN: SULINDAC], p-2-thenoylhydratropic acid [INN: SUPROFEN] 2-(4-(3-methyl-2-butenyl)phenyl)propionic acid [Research Code: TA-60], phthalidyl 2-(alpha,alpha,alpha-trifluoro-m-toluidino)nicotinate. [INN: TALNIFLUMATE], (Z)-5-chloro-3-(2-thenoyl)-2-oxoindole-1-carboxamide [INN: TENIDAP], 2-thiophenecarboxylic acid, ester with salicylic acid. [INN: TENOSAL], 4-hydroxy-2-methyl-N-2-pyridyl-2H-thieno[2,3-e]-1,2-thiazine-3-carboxamide [INN: TENOXICAM], 5-(4-chlorophenyl)-N-hydroxy-1-(4-methoxyphenyl)-N-methyl-1H-pyrazole-3-propionamide [INN: TEPOXALIN], alpha-(5-benzoyl-2-thienyl)propionic acid [INN: TIAPROFENIC ACID], 5-chloro-3-[4-(2-hydroxyethyl)-1-piperazinyl]carbonylmethyl-2-benzo-thiazolin one [INN: TIARAMIDE], 2-(2-methyl-5H-[1]benzopyrano[2,3-b]pyridin-7-yl)-propionic acid N,N-dimethylcarbamoylmethyl ester [INN: TILNOPROFEN ARBAMEL], 1-Cyclohexyl-2-(2-methyl-4-quinolyl)-3-(2-thiazolyl)guanidine [INN: TIMEGADINE], 2-amino-6-benzyl-4,5,6,7-tetrahydrothieno[2,3-c]pyridine [INN: TINORIDINE], N-(3-chloro-o-tolyl)anthranilic acid [INN: TOLFENAMIC ACID], 1-methyl-5-(4-methylbenzoyl)-1H-pyrrole-2-acetic acid [INN: TOLMETIN], hydroxybis[alpha-methyl-4-(2-methylpropyl)benzene acetato-O]-aluminium. [Research Code: U-18573-G], N-(3-trifluoromethylphenyl)-anthranilic acid n-butyl ester [INN: UFENAMATE], 2-[4-[3-(hydroxyimino)cyclohexyl]phenyl]propionic acid [INN: XIMOPROFEN], 2-(10,11-dihydro-10-oxo-dibenz[b,f]thiepin-2-yl-propionic acid

[INN: ZALTOPROFEN], 2-[4-(2-thiazolyloxy)phenyl]-propionic acid [INN: ZOLIPROFEN] and their pharmaceutically acceptable derivatives.

In an eleventh aspect—which is an embodiment of the tenth aspect—there is provided a process for the preparation of a pharmaceutical composition which comprises mixing a first active ingredient which is a PDE4-inhibitor selected from cis-[4-Cyano-4-(3-cyclopentyloxy-4-methoxyphenyl)cyclohexane-1-carboxylic acid [INN: CILOMILAST], 3-Cyclopropylmethoxy-4-difluoromethoxy-N-(3,5-dichloropyrid-4-yl)-benzamide [INN: ROFLUMILAST] and their pharmaceutically acceptable derivatives, with a second active ingredient which is a conventional NSAID selected from 2-(acetyloxy)benzoic acid [ACETYLSALICYLIC ACID], 2-[(2,6-dichlorophenyl)amino]benzeneacetic acid [INN: DICLOFENAC], alpha-p-isobutylphenylpropionic acid [INN: IBUPROFEN], 1-(4-chlorobenzoyl)-5-methoxy-2-methyl-1H-indole-3-acetic acid [INN: INDOMETACIN], (plus)-6-methoxy-alpha-methyl-2-naphthalineacetic acid [INN: NAPROXEN], 4-hydroxy-2-methyl-N-2-pyridyl-2H-1,2-benzothiadiazin-3-carboxamide 1,1-dioxide [INN: PIROXICAM] and their pharmaceutically acceptable derivatives.

In an twelfth aspect—which is another embodiment of the tenth aspect—there is provided a process for the preparation of a pharmaceutical composition which comprises mixing a first active ingredient which is selected from 3-Cyclopropylmethoxy-4-difluoromethoxy-N-(3,5-dichloropyrid-4-yl)-benzamide [INN: ROFLUMILAST] and its pharmaceutically acceptable derivatives, with a second active ingredient which is selected from 2-[(2,6-dichlorophenyl)amino]benzeneacetic acid [INN: DICLOFENAC] and its pharmaceutically acceptable derivatives.

The present invention further provides the use of a pharmaceutical composition, or pharmaceutical product according to the invention in the manufacture of a medicament for the treatment of an inflammatory disease and/or an inflammation associated disorder.

In a further aspect the present invention provides a method of an effective treatment of an inflammatory disease and/or an inflammation associated disorder which can be treated with a conventional NSAID while minimizing gastrointestinal side effects comprising the simultaneous, sequential or separate administration of i) a first amount of a conventional NSAID or a pharmaceutically acceptable derivative thereof; and ii) a second amount of a PDE4 inhibitor or a pharmaceutically acceptable derivative thereof, wherein the sum of the first and the second amount is a therapeutically effective amount, to a patient in need thereof.

In a still further aspect the present invention provides a method of minimizing gastrointestinal side effects frequently associated with the use of conventional NSAIDs comprising the simultaneous, sequential or separate administration of i) a first amount of a conventional NSAID or a pharmaceutically acceptable derivative thereof; and ii) a second amount of a PDE4 inhibitor or a pharmaceutically acceptable derivative thereof, wherein the sum of the first and the second amount is a therapeutically effective amount, to a patient in need thereof.

Said methods also include a pharmaceutical product or kit containing a conventional NSAID and a written description which discloses that said conventional NSAID can be administered together with a PDE4 inhibitor (a) for the treatment of an inflammatory disease and/or an inflammation associated disorder while minimizing gastrointestinal side effects or (b) for the attenuation of gastrointestinal side effects frequently associated with the use of conventional NSAIDs. Likewise, said methods include a pharmaceutical product or kit containing a PDE4 inhibitor and a written description which discloses that said PDE4 inhibitor can be administered together with a conventional NSAID (a) for the treatment of an inflammatory disease and/or an inflammation associated disorder while minimizing gastrointestinal side effects or (b) for the attenuation of gastrointestinal side effects frequently associated with the use of conventional NSAIDs.

"Inflammatory diseases" which may be mentioned in particular are arthritis, including but not limited to rheumatoid arthritis, osteoarthritis, systemic lupus erythematosus and juvenile arthritis; gastrointestinal conditions such as inflammatory bowel disease, Crohn's disease, irritable bowel syndrome and ulcerative colitis; asthma, bronchitis and skin related disorders such as psoriasis, eczema, burns and dermatitis.

"Inflammation associated disorders" which may be mentioned are, for example, pain, migraine, fever and headaches.

The active ingredients may, and indeed will, as part of the pharmaceutical composition, the pharmaceutical product or preparation, be used in admixture with one or more pharmaceutically acceptable auxiliaries and/or excipients.

The person skilled in the art is familiar on the basis of his/her expert knowledge with which excipients or auxiliaries are suitable for the desired pharmaceutical composition, product or preparation. In addition to solvents, gel-forming agents, tablet excipients and other active compound carriers, it is possible to use, for example, antioxidants, dispersants, emulsifiers, antifoams, flavor corrigents, preservatives, solubilizers, colorants or permeation promoters and complexing agents (e.g. cyclodextrins).

Within the meaning of the present invention, "combined use" is preferably understood as meaning the oral administration of both active ingredients. Further methods of administration, which may be mentioned are the parenteral (for example intravenous injection or infusion or intramuscular or intraarticular injection) and the topical administration of the active ingredients.

For oral administration the pharmaceutical compositions or products according to the invention are preferably in the form of tablets, coated tablets, chewing tablets, lemonade tablets, dragees, capsules, caplets, suppositories, emulsions, (sterile parenteral) suspensions or solutions, the active ingredient content advantageously being between 0.1 and 95% and by appropriate choice of the excipients and the auxiliaries, it being possible to achieve a pharmaceutical administration form precisely tailored to the active ingredient(s) and/or to the desired onset of action (e.g. a sustained release form or an enteric form).

For the treatment of diseases of the arthritic type or skin related disorders, the compounds according to the invention also can be used in form of pharmaceutical compositions or products which are suitable for topical application. For the production of those pharmaceutical compositions or products, the compounds according to the invention (=active ingredients) are preferably mixed with suitable pharmaceutical excipients and further processed to give suitable pharmaceutical formulations. Suitable pharmaceutical formulations which may be mentioned in this connection are, for example, ointments, fatty ointments, creams, pastes or gels. The pharmaceutical compositions or products for topical application can preferably also be in form of a patch (e.g. as TTS).

For the above-mentioned therapeutic uses the dosages administered will, of course, vary with the first and second active ingredients employed, the mode of administration, the treatment desired and the disorder indicated.

However, in general, satisfactory results will be obtained when the total daily dosage of first active ingredient(s), the PDE4 inhibitor(s), when taken oral is in the range from 1-2000 μg/kg of body weight. In the case of the especially preferred PDE4 inhibitor ROFLUMILAST, the daily dosage is in a range from 2-20 μg/kg of body weight.

The total daily dosage of the second active ingredient(s), the conventional NSAIDs also can vary within a wide range. In the case of the especially preferred NSAIDs Diclofenac the daily doses are in a range from 100-200 μg/kg.

Pharmacology

Investigations into the role of several NSAIDs in inhibiting the phosphodiesterase 4 and 5 in vitro (Table 1 below) showed that in partially purified or recombinant PDE4 and PDE5, NSAIDs with preferential COX-2 selectivity (for example, nimesulide [INN], CGP28238 [Research Code], L-745337 [Research Code], and the highly selective drug celecoxib [INN]) possess PDE4 and PDE5 activity in the μM range, whereas conventional NSAIDs (for example, acetylsalicylic acid, diclofenac [INN] or indometacin [INN]) show only minor effects:

TABLE 1

| | ($IC_{50}$, μM) | | | | | |
|---|---|---|---|---|---|---|
| | ASS | Diclofenac | Indometacin | Nimesulide | CGP28238 | L-745337 | Celecoxib |
| PDE4 | >100 | >100 | ~100 | 58 | 23 | 31 | 6 |
| PDE5 | >100 | >100 | 62 | 25 | 14 | 24 | 12 |

ASS, acetylsalicylic acid; diclofenac, 2-[(2,6-dichlorophenyl)amino]benzeneacetic acid; indomethacin, 1-(4-chlorobenzoyl)-5-methoxy-2-methyl-1H-indole-3-acetic acid; nimesulide, 4'-nitro-2'-phenoxymethansulfonamide; CGP28238, 6-(2,4-difluorophenoxy)-5-methylsulfonylamino-1-indanone; L-745337 5-methanesulfonamido-6-(2,4-difluorophenylthio)-1-indanone); celecoxib, (4-[5-(4-methylphenyl)-3-(tri-fluoromethyl)-1H-pyrazol-1-yl] benzenesulfonamide.

In isolated guinea pig Langendorff hearts, celecoxib selectively increased coronary heart flow at doses consistent with its inhibitory potency on PDE4 and 5, but had no effect on left ventricular pressure and heart rate, thereby excluding inhibition of PDE3.

In mice, diclofenac (3-100 mg/kg, p.o.) induced gastrointestinal bleeding ($ED_{50}$=56 mg/kg), assessed by spectrophotometric determination of fecal hemoglobin. Treatment with diclofenac (10-100 mg/kg, p.o. t=0 h) in the presence of the selective PDE5 inhibitor sildenafil (3-100 mg/kg, p.o. t=−48 h to +7 h) demonstrated no protection from NSAID-induced blood loss, whereas treatment in the presence of several selective PDE4 inhibitors significantly reduced the amount of detectable hemoglobin.

Influence of PDE4 Inhibition on Diclofenac Induced Blood Loss in Mice

Methods

In Vivo Experiments

Male NMRI mice (Charles River Laboratories, Sulzfeld, Germany) weighting 23-25 g were housed in groups of 5 under standard conditions at a temperature of 22° C.+/−2° C. and a 12 h light-dark cycle. If not otherwise stated animals had free access to tap water and standard food pellets. Diclofenac was administrated at doses from 1-100 mg/kg p.o.; rolipram, roflumliast and RP73401 were given at doses from 1-100 mg/kg p.o. Preventive treatment: Diclofenac was given at time point 0 h. At time points −24, −16, 0 h, +7 h one of the selective PDE4 inhibitors was administered. Curative treatment: Diclofenac was given at time point 0 h. At time points +1 h and +7 h one of the selective PDE4 inhibitors was administered. The drugs used were dissolved in 4% aqueous methyl cellulose. The animals were food reduced 24 h prior diclofenac administration. For each experiment 5 animals were used for one experimental point. Following 24 h administration of drugs animals were weighted and stool was collected quantitatively and homogenized as described below:

Detection of Hemoglobin in Feces

The modified method of Welch (Clin. Chem. 29/12, 2022-2025, 1983) was used. The amount of hemoglobin was determined by the heme catalyzed oxidation of tolidine in the presence of hydrogen peroxide. Feces was homogenized in destined water in a concentration with 1 g feces/6.6 ml H20 with an ultra-turrax (IKA-Werke, Germany). 500 μl aliquots from two different areas of the stool were taken to minimize error due to inhomogenous distribution of blood in the feces and heated 10 min at 95° C. to inactivate peroxidases and than diluted with 500 μl of acetic acid/H20 (30/70 vol/vol). Hemoglobin was extracted in 2.5 ml of acetic acid/H20 (30/70 vol/vol) by the addition of 4.5 ml ethyl acetate. The sample was rigorously shacked and the supernatant was used following a centrifugation step for optical detection of hemoglobin. Tolidine was prepared freshly from a stock solution (0.4 g tolidine in 10 ml ethanol) by mixing equal volumes of stock solution, H20 and acetic acid and equilibrated at room temperature. 20 μl of extracted supernatant was diluted to 100 μl ethyl acetate in a 96er crystal plate and incubated with 50 μl of the working solution. The reaction was initiated by the injection of 25 μl hydrogen peroxide (6%) in a Wallac Victor spectro-photometer (Turku, Finnland). The increase of OD 690 was monitored by a kinetic analysis and expressed as $\Delta OD690$/min.

Results

Table 2 shows the % reduction of the $\Delta OD_{690}$/min when a PDE4 inhibitor was administered (preventive or curative) compared to the $\Delta OD_{690}$/min obtained without the administration of a PDE4-inhibitor.

TABLE 2

| | [% reduction of $\Delta OD_{690}$/min] | |
|---|---|---|
| | NSAID: 100 mg/kg diclofenac | NSAID: 30 mg/kg indometacin |
| Rolipram 30 mg/kg (preventive) | 90% | |
| Rolipram 10 mg/kg (curative) | 82% | |
| Roflumilast 10 mg/kg (preventive) | 95% | |
| Roflumilast 3 mg/kg (curative) | 95% | |

TABLE 2-continued

| | [% reduction of $\Delta OD_{600}$/min] | |
| --- | --- | --- |
| | NSAID: 100 mg/kg diclofenac | NSAID: 30 mg/kg indomethacin |
| Rolipram 100 mg/kg (curative) | | 65% |
| RP73401 100 mg/kg (curative) | | 96% |

The invention claimed is:

1. A method of minimizing gastrointestinal side effects frequently associated with the use of conventional NSAIDs comprising the simultaneous, sequential or separate administration to a patient in need thereof of
(i) a first amount of 2-(2,6- dichlorophenyl) amino]benzeneacetic acid [INN: DICLOFENAC] or a pharmaceutically acceptable salt, ester, solvate, solvate of a salt, or solvate of an ester thereof; and
(ii) a second amount of 3-Cyclopropylmethoxy-4-difluoromethoxy-N-(3,5-dichloro pyrid-4- yl)-benzamide [INN: ROFLUMILAST] or a pharmaceutically acceptable salt, solvate, N-oxide, solvate of a salt, or solvate of an N-oxide thereof;
wherein the sum of the first and second amounts is a therapeutically effective amount.

2. The method according to claim 1 wherein (i) and (ii) are administered (A) simultaneously as a fixed dosage form, or (B) simultaneously, sequentially, or separately as discrete separate dosage forms.

3. The method according to claim 1 wherein the method is used in the treatment of an inflammatory disease.

4. The method according to claim 3 wherein the inflammatory disease is rheumatoid arthritis, osteoarthritis, systemic lupus erythematosus, juvenile diabetes, inflammatory bowel disease, Crohn's disease, irritable bowel syndrome, or ulcerative colitis.

* * * * *